US010711046B2

(12) United States Patent
Wu et al.

(10) Patent No.: US 10,711,046 B2
(45) Date of Patent: Jul. 14, 2020

(54) METHOD FOR ESTABLISHING EUKARYOTIC EXPRESSION CELL LINE OF CD36 MUTANT GENE THAT ENCODES CD36 DEFICIENCY

(71) Applicant: Nan-Ning Institute of Transfusion Medicine, Nanning (CN)

(72) Inventors: Guoguang Wu, Nanning (CN); Lilan Li, Nanning (CN); Lihong Jiang, Nanning (CN); Haiyan Li, Nanning (CN); Jierun Chen, Nanning (CN)

(73) Assignee: NAN-NING INSTITUTE OF TRANSFUSION MEDICINE, Nanning (CN)

( * ) Notice: Subject to any disclaimer, the term of this patent is extended or adjusted under 35 U.S.C. 154(b) by 0 days.

(21) Appl. No.: 16/188,187

(22) Filed: Nov. 12, 2018

(65) Prior Publication Data

US 2019/0062387 A1 Feb. 28, 2019

Related U.S. Application Data

(63) Continuation-in-part of application No. PCT/CN2017/075785, filed on Mar. 6, 2017.

(30) Foreign Application Priority Data

Nov. 1, 2016 (CN) .......................... 2016 1 0967814

(51) Int. Cl.

*C07K 14/47* (2006.01)
*C12N 15/85* (2006.01)
*C12N 15/65* (2006.01)
*C12N 5/071* (2010.01)
*C12N 9/00* (2006.01)
*C12Q 1/6806* (2018.01)
*C12Q 1/6876* (2018.01)
*C12Q 1/686* (2018.01)
*C07K 14/705* (2006.01)

(52) U.S. Cl.

CPC ...... *C07K 14/473* (2013.01); *C07K 14/70596* (2013.01); *C12N 5/0602* (2013.01); *C12N 9/93* (2013.01); *C12N 15/65* (2013.01); *C12N 15/85* (2013.01); *C12Q 1/6806* (2013.01); *C12Q 1/686* (2013.01); *C12Q 1/6876* (2013.01); *C12N 2740/15043* (2013.01); *C12N 2740/16043* (2013.01); *C12Y 605/01001* (2013.01)

(58) Field of Classification Search

CPC .. C07K 14/70596; C07K 14/473; C12N 9/93; C12N 15/65; C12Q 1/686

See application file for complete search history.

(56) References Cited

FOREIGN PATENT DOCUMENTS

EP 1162458 A1 12/2001

OTHER PUBLICATIONS

L.L. Li et al., A novel CD36 mutation T538C (Trp180Arg) results in CD36 deficiency and establishment of a genotyping method for the novel mutation based on Sequence-Specific Primer PCR, Chinese Journal of Medical Genetics, Oct. 2016, pp. 619-624, vol. 33, No. 5, Chinese Medical Association, Chengdu, China.

H. Kashiwagi et al., Analyses of genetic abnormalities in type I CD36 deficiency in Japan: identification and cell biological characterization of two novel mutations that cause CD36 deficiency in man, Human Genetics, Jun. 30, 2001, pp. 459-466, vol. 108, No. 6, Springer-Verlag, Berlin, Germany.

X.Z. Xu et al., Establishment of a cell line expressing the CD36 on human platelets and its application to the detection of anti-CD36 antibodies, Chinese Journal of Microbiology and Immunology, Jun. 2016, pp. 458-462, vol. 36, No. 6, Chinese Medical Association, Beijing, China.

G.G. Wu et al., Homo sapiens mutant thrombospondin receptor (CD36) gene, partial cds, GenBank, Nov. 24, 2013, Database accession No. KF539919.1, National Center for Biotechnology Information, United States.

G.G. Wu et al., Homo sapiens cell-line YSQ platelet glycoprotein IV variant (CD36) mRNA, complete cds, GenBank, Jun. 21, 2010, Database accession No. HM217022.1, National Center for Biotechnology Information, United States.

W. Wei et al., Amplification of long DNA fragment by splicing overlap extension PCR, Journal of Yunnan University (Natural Sciences Edition), 2008, pp. 86-88, vol. 30, No. S1, China Academic Journal Electronic Publishing House, China.

W. Xia et al., CD36 deficiency among South-East Asian populations, ISBT Science Series, Jun. 2016, pp. 33-36, vol. 11, No. S2, Wiley, United States.

*Primary Examiner* — Antonio Galisteo Gonzalez

(74) *Attorney, Agent, or Firm* — Matthias Scholl P.C.; Matthias Scholl

(57) ABSTRACT

A method for establishing eukaryotic expression cell line of CD36 mutant gene that encodes CD36 deficiency, the method including: (1) extracting total RNA from a whole blood sample derived from a CD36-deficient individual, and amplifying a coding sequence (CDS) in CD36 mRNA, to obtain a cDNA sequence fragment of the mutant CD36 gene; (2) splicing and amplifying the mutant CD36 gene and the EGFP fluorescent gene by SOE-PCR (Gene Splicing By Overlap Extension PCR) using four forward and reverse primers, to obtain a mutant gene fragment of MT-CD36-EGFP; (3) constructing and amplifying a MT-CD36-EGFP-pLV4/StripII-HIS10 eukaryotic expression vector including the mutant CD36 gene and the EGFP fluorescent gene; (4) transfecting the MT-CD36-EGFP-pLV4/StripII-HIS10 eukaryotic expression vector into the CHO-K1 cell line by using virus-mediated transfection of eukaryotic cells.

3 Claims, 10 Drawing Sheets

Specification includes a Sequence Listing.

SEQUENCE LISTING

```
<160> NUMBER OF SEQ ID NOS: 11

<210> SEQ ID NO 1
<211> LENGTH: 25
<212> TYPE: DNA
<213> ORGANISM: Homo sapiens

<400> SEQUENCE: 1

atcctcgaga tgggctgtga ccgga                                           25


<210> SEQ ID NO 2
<211> LENGTH: 27
<212> TYPE: DNA
<213> ORGANISM: Homo sapiens

<400> SEQUENCE: 2

gcagaattcg ttttattgtt ttcgatc                                         27


<210> SEQ ID NO 3
<211> LENGTH: 28
<212> TYPE: DNA
<213> ORGANISM: Homo sapiens

<400> SEQUENCE: 3

ccggaattca tgggctgtga ccggaact                                        28


<210> SEQ ID NO 4
<211> LENGTH: 39
<212> TYPE: DNA
<213> ORGANISM: Homo sapiens

<400> SEQUENCE: 4

tgctcaccat ggatccgcgt tttattgttt tcgatctgc                            39


<210> SEQ ID NO 5
<211> LENGTH: 39
<212> TYPE: DNA
<213> ORGANISM: Aequorea victoria

<400> SEQUENCE: 5

aacaataaaa cgcggatcca tggtgagcaa gggcgagga                            39


<210> SEQ ID NO 6
<211> LENGTH: 31
<212> TYPE: DNA
<213> ORGANISM: Aequorea victoria

<400> SEQUENCE: 6

ccgctcgagc cgctttactt gtacagctcg t                                    31
```

-continued

```
<210> SEQ ID NO 7
<211> LENGTH: 29
<212> TYPE: DNA
<213> ORGANISM: Aequorea victoria

<400> SEQUENCE: 7

ccggaattca tggtgagcaa gggcgagga                                      29


<210> SEQ ID NO 8
<211> LENGTH: 25
<212> TYPE: DNA
<213> ORGANISM: Homo sapiens

<400> SEQUENCE: 8

gtgcaaaatc cayaggaagt gatga                                          25


<210> SEQ ID NO 9
<211> LENGTH: 20
<212> TYPE: DNA
<213> ORGANISM: Homo sapiens

<400> SEQUENCE: 9

gcaaaatcca taggaagtga                                                20


<210> SEQ ID NO 10
<211> LENGTH: 20
<212> TYPE: DNA
<213> ORGANISM: Homo sapiens

<400> SEQUENCE: 10

gcaaaatcca taggaagtga                                                20


<210> SEQ ID NO 11
<211> LENGTH: 20
<212> TYPE: DNA
<213> ORGANISM: Homo sapiens

<400> SEQUENCE: 11

gcaaaatcca taggaagtga                                                20
```

METHOD FOR ESTABLISHING EUKARYOTIC EXPRESSION CELL LINE OF CD36 MUTANT GENE THAT ENCODES CD36 DEFICIENCY

CROSS-REFERENCE TO RELATED APPLICATIONS

This application is a continuation-in-part of International Patent Application No. PCT/CN2017/075785 with an international filing date of Mar. 6, 2017, designating the United States, now pending, and further claims foreign priority benefits to Chinese Patent Application No. 201610967814.1 filed Nov. 1, 2016. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The disclosure relates to biomedicine, and, in particular, to a method for establishing eukaryotic expression cell line of CD36 mutant gene that encodes CD36 deficiency.

Description of the Related Art

CD36 (Leukocyte Differentiation Antigen 36), also known as Platelet Glycoprotein IV (GPIV), GP88, GPIIIb, FAT or SCARB3, belongs to the Class B scavenger receptor family of transmembrane glycoproteins. The human CD36 protein consists of 472 amino acids, and mainly functions to act as a thrombin receptor, a collagen receptor, a long-chain fatty acid receptor, a receptor for selective cholesteryl ester uptake, a lysosome membrane protein II receptor, etc.; and it is also involved in inducing apoptosis, removing oxidized low-density lipoproteins in the plasma, and enhancing cytoadherence of abnormal shaped red blood cells, etc. CD36 plays an important role in a variety of pathophysiological processes by binding to various ligands and interacting with many ligands, as well as by serving as adhesion molecules on the cell surface. Numerous studies have demonstrated that CD36 is involved in the development of hemostasis, thrombosis, alloimmune platelet disorders, hypercholesterolemia, obesity, peripheral atherosclerosis, arterial hypertension, cardiomyopathy, diabetes, malaria, presenile dementia (Alzheimer's disease) and other diseases.

Some healthy individuals may have CD36 deficiency in platelets and monocytes, which can be divided into two types according to the phenotype: type I CD36 deficiency, in which no CD36 is expressed on platelets and monocytes, and type II CD36 deficiency, in which CD36 is expressed not on platelets, but on monocytes.

The variation of human CD36 gene is an important reason leading to the deficiency of CD36 antigen. The molecular basis underlying the mutant CD36 genes that have been reported to cause CD36 protein deficiency can be substantially divided into two types: (1) insertion or deletion mutations, which mainly cause frameshift or exon skipping; and (2) single nucleotide polymorphism (SNP), which causes amino acid substitutions.

Numerous studies have shown that the low or absence of CD36 expression on human cells and tissues is closely related to the development and severity of various CD36-related diseases, especially, that has direct influence on the development and severity of malaria, hypercholesterolemia, obesity, peripheral atherosclerosis, cardiomyopathy, diabetes, pre-senile dementia and other diseases. In CD36-deficient individuals, the CD36 protein can act as an isoantigen to immunize the CD36-deficient individuals to produce an anti-CD36 isoantibody through blood transfusion, pregnancy and bone marrow transplantation, leading to the occurrence of clinical problems including immune refractoriness to platelet transfusion, post-transfusion purpura, fetal/neonatal alloimmune thrombocytopenia, passive alloimmune thrombocytopenia, and various other types of alloimmune platelet abnormalities.

Until now, most of the reported studies on mutant CD36 genes that cause CD36 deficiency have focused on the cDNA sequencing and prokaryotic cloning of the CD36 gene. There have been no reports on methods for establishing eukaryotic cell lines stably expressing the mutant CD36 gene leading to human CD36 deficiency.

SUMMARY OF THE INVENTION

One object of the disclosure is to provide a method for establishing a eukaryotic cell line stably expressing mutant CD36 gene. The method is also applicable to the establishment of a eukaryotic cell line stably expressing normal CD36 gene. By means of the establishment method, the problems of permanent and stable preservation and preparation of various CD36 mutant genes and expressed proteins are solved; an infinitely valuable genetic resources is provided for studying the molecular structure and functions of CD36, elucidating the mechanism of action of CD36 in various physiological and pathological processes in human and further for deep insight into the important role of CD36 in clinical medicine; a high-quality work platform is provided for the development of drugs and screening of drug targets in the treatment of CD36-related hemostasis, thrombosis, alloimmune platelet disorders, hypercholesterolemia, obesity, peripheral atherosclerosis, arterial hypertension, cardiomyopathy, diabetes, malaria, presenile dementia (Alzheimer's disease) and other diseases; and the established cell line can be directly used as a panel cell for detecting anti-CD36 antibodies causing platelet transfusion refractoriness, to ensure the safety and efficacy of platelet transfusion therapy.

To achieve the above objects, the disclosure provides a method for establishing eukaryotic stable expression cell line of CD36 mutant gene that encodes CD36 deficiency. The method comprises:

(1) extracting total RNA from a whole blood sample derived from a CD36-deficient individual, and amplifying the coding sequence (CDS) in CD36 mRNA by Reverse Transcription PCR (RT-PCR) using a pair of primers for RT-PCR amplification, to obtain a cDNA sequence fragment of the mutant CD36 gene that encodes CD36 deficiency, wherein the primers for RT-PCR amplification comprise an upstream primer YC-36F having a sequence of 5'-ATC CTC GAG ATG GGC TGT GAC CGG A-3' (SEQ. ID. NO. 1), and a downstream primer YC-36R having a sequence of 5'-GCA GAA TTC GTT TTA TTG TTT TCG ATC-3' (SEQ. ID. NO. 2);

(2) splicing and amplifying the mutant CD36 gene and the EGFP fluorescent gene by SOE-PCR (Gene Splicing by Overlap Extension PCR) using four forward and reverse primers, to obtain a mutant gene fragment of MT-CD36-EGFP comprising the full-length cDNA encoding region of the mutant CD36 gene, the full-length EGFP fluorescent gene and desired restriction enzyme cleveagesites, wherein the primers for SOE-PCR comprises:

a forward primer CD36-F2 and a reverse primer CD36-R3 for amplification to obtain a target gene fragment of MT-CD36-EGFP-1 comprising an EcoR 1 cleavage site and protective bases, a full-length coding sequence (CDS) excluding the terminator of CD36 cDNA, a fusion gene BamH I and protective bases, and a portion of the 5'-terminal sequence of the EGFP fluorescent reporter gene, wherein the forward primer CD36-F2 also serves as a forward primer for the subsequent splicing and amplification of MT-CD36-EGFP by SOE-PCR, and has a sequence of 5'-CCG GAA TTC ATG GGC TGT GAC CGG AAC T-3' (SEQ. ID. NO. 3), and the reverse primer CD36-R3 has a sequence of 5'-TGC TCA CCA TGG ATC CGC GTT TTA TTG TTT TCG ATC TGC-3' (SEQ. ID. NO. 4); and a forward primer EGFP-F4 and a reverse primer EGFP-R2 for amplification to obtain a target gene fragment of MT-CD36-EGFP-2 comprising a portion of the 3'-terminal fragment of the CD36 coding region cDNA, a fusion gene BamH I and protective bases, a full-length gene sequence of the EGFP fluorescent reporter gene, and an XhoI cleavage site and protective bases, wherein the reverse primer EGFP-R2 also serves as a reverse primer for the subsequent splicing and amplification of MT-CD36-EGFP by SOE-PCR, wherein the forward primer EGFP-F4 has a sequence of 5'-AAC AAT AAA ACG CGG ATC CAT GGT GAG CAA GGG CGA GGA-3' (SEQ. ID. NO. 5), and the reverse primer EGFP-R2 has a sequence of 5'-CCG CTC GAG CCG CTT TAC TTG TAC AGC TCG T-3' (SEQ. ID. NO. 6);

(3) constructing and amplifying a MT-CD36-EGFP-pLV4/StripII-HIS10 eukaryotic expression vector comprising the mutant CD36 gene and the EGFP fluorescent gene by ligating MT-CD36-EGFP to a pLV4/StripII-HIS10 vector;

(4) transfecting the MT-CD36-EGFP-pLV4/StripII-HIS10 eukaryotic expression vector into the CHO-K1 cell line by using virus-mediated transfection of eukaryotic cells, and screening and constructing a eukaryotic cell line MT-CD36-CHO-K1 stablely expressing the mutant CD36 gene that encodes CD36 deficiency; and (5) by using the method of the present disclosure, establishing a eukaryotic cell line Normal-CD36-CHO-K1 stably expressing normal CD36 gene as a positive control, and establishing a EGFP-pLV4-CHO-K1 line stably expressing the EGFP fluorescent protein alone as a negative control, wherein in the construction of the negative control EGFP-pLV4-CHO-K1 line, a target gene fragment encoding EGFP comprising an EcoR 1 cleavage site and protective bases, the full-length gene sequence of the EGFP fluorescent reporter gene, and an XhoI cleavage site and protective bases is obtained by amplification using a pair of PRC primers, wherein the PCR primers comprise an upstream primer EGFP-F3 having a sequence of 5'-CCG GAA TTC ATG GTG AGC AAG GGC GAG GA-3' (SEQ. ID. NO. 7), and a downstream primer EGFP-R2 that is the reverse primer for amplification of the gene fragment of MT-CD36-EGFP-2 as described in (2)

Specific description of the method according to the present disclosure:

1. In step (1), the primers for amplifying the cDNA of the mutant CD36 gene (MT-CD36 cDNA) by RT-PCR comprises the upstream primer YC-36F and the downstream primer YC-36R, where the upstream primer YC-36F has a sequence of 5'-ATCCTCGAGATGGGCTGTGACCGGA-3' (SEQ. ID. NO. 1), and the downstream primer YC-36R has a sequence of 5'-GCAGAATTCGTTTTATTGTTTTCGATC-3'(SEQ. ID. NO. 2). The upstream primer YC-36F is located in a 5'-promoter region of the CD36 mRNA sequence, and the downstream primer YC-36R is located in a 3'-terminator region of the CD36 mRNA sequence. The amplification region covers the coding sequence (CDS) excluding the terminator of CD36 mRNA, and a plurality of mutant CD36 genes with mutations within a linker region of 5'-terminal and 3'-terminal primer binding regions of the template. If the target gene amplified is a mutant CD36 gene with point mutations, the length of the amplified fragment is 1432 bp, and if the target gene amplified is a mutant CD36 gene with base insertions or deletions, the length of the amplified fragment is increased or decreased on the basis of 1432 bp by the base number inserted or deleted. The RT-PCR amplification is carried out by using the TaKaRa One step RNA PCR Kit (AMV) (one-step method), where the reaction system has a composition of (the total volume of the reaction system is 50 μL):

| | |
|---|---|
| 10x one step RNA PCR Buffer | 5 μL |
| 25 mM MgCl2 | 10 μL |
| 10 mM dNTPs | 5 μL |
| Rnase Inhibitor (40 u/μL) | 1 μL |
| AMV Rtase XL | 1 μL |
| AMV-Optimized Taq | 1 μL |
| Primer YC-36F (20 μM) | 1 μL |
| Primer YC-36R (20 μM) | 1 μL |
| RNA (100-500 ng/μL) | 10 μL |
| $H_2O$ | 15 μL |

The cycling parameters comprise:

| | |
|---|---|
| 50° C. | 30 min |
| 94° C. | 2 min |
| 30 amplification cycles of: | |
| 94° C. | 30 sec |
| 60° C. | 30 sec |
| 72° C. | 2 min; and |
| extension and storage at: | |
| 72° C. | 10 min |
| 12° C. | ∞. |

The target fragment of MT-CD36 cDNA is sequenced.

2. In step (2), the primers for SOE-PCR comprise:

the forward primer CD36-F2 and the reverse primer CD36-R3 for amplification to obtain the target gene fragment of MT-CD36-EGFP-1 comprising an EcoR 1 cleavage site and protective bases, a full-length the coding sequence (CDS) excluding the terminator of CD36 cDNA, a fusion gene BamH I and protective bases, and a portion of the 5'-terminal sequence of the EGFP fluorescent reporter gene, where the forward primer CD36-F2 has a sequence of 5'-CCGGAATTCATGGGCTGTGACCGGAACT-3' (SEQ. ID. NO. 3), and the reverse primer CD36-R3 has a sequence of 5'-TGCTCACCATGGATCCGCGTTTTATTGTTTTCGATCTGC-3' (SEQ. ID. NO. 4), as schematically shown in FIG. 1; the forward primer CD36-F2 is located in a 5'-promoter region of the template, the reverse primer CD36-R3 is located in a 3'-terminal region excluding the terminator of the template; the amplification region covers the coding sequence (CDS) excluding the terminator of CD36 cDNA excluding the termination codons, the EcoR1 cleavage site at the 5' end, and a fusion gene BamH I and 10 bases comprising the promoter of the coding sequence (CDS) of EGFP at the 3' end; and for the length of the target fragment amplified, if the target gene amplified is a mutant CD36 gene with point mutations, the length of the amplified fragment is 1441 bp, and if the target gene amplified is a mutant CD36 gene with base insertions or deletions, the length of the amplified fragment is increased or decreased on the basis of 1441 bp by the base number inserted or deleted; and the forward primer EGFP-F4 and the reverse primer EGFP-R2 for amplification to obtain the target gene fragment of MT-CD36-EGFP-2 comprising a portion of the 3'-terminal fragment of the CD36 encoding cDNA region, a fusion gene BamH I and protective bases, a full-length gene sequence of the EGFP fluorescent reporter gene, and an XhoI cleavage site and protective bases, where the forward primer EGFP-F4 has a sequence of 5'-AACAATAAAACGCGGATCCATGGTGAG-CAAGGGCGAGGA-3' (SEQ. ID. NO. 5), and the reverse primer EGFP-R2 has a sequence of 5'-CCGCTCGAGC-CGCTTTACTTGTACAGCTCGT-3' (SEQ. ID. NO. 6), as schematically shown in FIG. 2; the 5' terminus of the EGFP-F4 comprises a 3'-terminal 10-base sequence before the terminator TAA of the CD36 cDNA sequence and the fusion gene BamH I and protective bases; the amplification region covers the full length sequence comprising the promoter and the terminator of the EGFP CDS, the 3'-terminal 10-base sequence excluding the terminator of the CD36 protein encoding cDNA region at 5' end of the amplification region, and the XhoI cleavage site at 3' end of the amplification region; and the length of the amplified target fragment is 753 bp.

The reaction system for PCR amplification to obtain the gene fragment of MT-CD36-EGFP-1 by using MT-CD36 cDNA obtained in step (1) as a template and using the CD36-F2 and CD36-R3 respectively as a forward and reverse primer has a composition of (the total volume of the reaction system is 25 μL):

| | |
|---|---|
| *dd*$H_2O$ | 15 μL |
| 5 × SF Buffer (with 10 mM MgCl2) (Vazyme) | 5 μL |
| dNTP mix (10 mM each) | 0.5 μL |
| CD36-F2 (10 μM) | 1 μL |
| CD36-R3 (10 μM) | 1 μL |
| MT-CD36 cDNA | 1 μL |
| DMSO | 1 μL |
| HS suffer-Fieviy DNA polymerase (Vazyme) | 0.5 μL |

The reaction system for PCR amplification to obtain the gene fragment of MT-CD36-EGFP-2 by using the eukaryotic plasmid pEGFP-N1 containing the EGFP fluorescent reporter gene (Suzhou Genepharma Co., Ltd) as a template and using the EGFP-F4 and EGFP-R2 respectively as a forward and reverse primer has a composition of (the total volume of the reaction system is 25 μL):

| | |
|---|---|
| *dd*$H_2O$ | 16 μL |
| 5 × SF Buffer (with 10 mM MgCl2) (Vazyme) | 5 μL |
| dNTP mix (10 mM each) | 0.5 μL |
| EGFP-F4 (10 μM) | 0.5 μL |
| EGFP-R2 (10 μM) | 0.5 μL |
| pEGFP-N1 plasmid | 1 μL |
| DMSO | 1 μL |
| HS suffer-Fieviy DNA polymerase (Vazyme) | 0.5 μL |

The cycling parameters for PCR amplification of the gene fragments of MIT-CD36-EGFP-1 and MT-CD36-EGFP-2 comprise:

| | |
|---|---|
| 96° C. | 5 min |
| 33 amplification cycles of: | |
| 96° C. | 30 sec |
| 60° C. | 30 sec |
| 72° C. | 90 sec; and |
| extension and storage at: | |
| 72° C. | 10 min |
| 12° C. | ∞. |

By using MT-CD36-EGFP-1 and MT-CD36-EGFP-2 obtained through PCR amplification as templates, and using the forward primer CD36-F2 and the reverse primer EGFP-R2, the gene fragment of MT-CD36-EGFP comprising the full-length cDNA encoding region of the mutant CD36 gene, a fusion gene BamH I and protective bases, the full-length fragment of the EGFP fluorescent gene, and desired EcoR1 and XhoI cleavage sites is obtained by splicing and amplification of the mutant CD36 gene and the EGFP fluorescent gene by SOE-PCR. The amplification region covers the EcoR1 cleavage site and protective bases, the CDS excluding the terminator of CD36 cDNA, the fusion gene BamH I and protective bases, the full length fragment of the EGFP CDS, and the XhoI cleavage site and protective bases. For the length of the target fragment amplified, if the target gene amplified is a mutant CD36 gene with point mutations, the length of the amplified fragment is 2165 bp, and if the target gene amplified is a mutant CD36 gene with base insertions or deletions, the length of the amplified fragment is increased or decreased on the basis of 2165 bp by the base number inserted or deleted. The reaction system comprises:

| | |
|---|---|
| $H_2O$ | 24 μL |
| 5 × SF Buffer (with 10 mM MgCl2) (phanta ™) | 10 μL |
| dNTP Mix (10 mM each) | 1 μL |
| MT-CD36-EGFP-1 | 4 μL |
| MT-CD36-EGFP-2 | 4 μL |
| phanta ™HS Suffer-Fideliy DNA Polymerase | 1 μL |

The cycling parameters comprise:

| | |
|---|---|
| 98° C. | 5 min |
| 15 amplification cycles of: | |
| 98° C. | 5 min |
| 72° C. | 1 min. |

A system having the following composition is added to the reaction tube after the reaction is completed:

| | |
|---|---|
| CD36-F2 (10 μM) | 2 μL |
| EGFP-R2 (10 μM) | 2 μL |
| DMSO | 2 μL |

Amplification is continued through a process which is performed under the following cycling parameters:

| | |
|---|---|
| 20 amplification cycles of: | |
| 98° C. | 10 sec |
| 56° C. | 30 sec |
| 72° C. | 60 sec; and |

-continued

| extension and storage at: | |
|---|---|
| 72° C. | 10 min |
| 12° C. | ∞. |

The product MT-CD36-EGFP (as schematically shown in FIG. 3) obtained by SOE-PCR amplification is subjected to 1.5% agarose gel electrophoresis (105 v, 40 min), gel cutting, and gel extraction by using the AxyPrep DNA Gel Extraction Kit (AXYGEN). The extracted product is sequenced, to confirm that the amplified product is consistent in sequence with the target fragment. Then, the extracted product is used in the construction of the eukaryotic expression vector in step (3).

3. In step (3), the target gene fragment of MT-CD36-EGFP obtained in step (2) that was purified by gel extraction and the eukaryotic vector pLV4/StripII-HIS10 (Shenzhen Angran Biotechnology Co., Ltd.) are enzymatically cleaved by using the EcoR1/Xhol DNA Endonuclease Kit (Beyotime Biotechnology), in which the reaction system comprises (the total volume of the reaction system is 20 μL):

| | |
|---|---|
| MT-CD36-EGFP or eukaryotic vector pLV4/StripII-HIS10 | 14 μL |
| 10 × Buffer Y | 2 μL |
| ECOR 1 | 1 μL |
| Xhol | 1 μL |
| *dd*$H_2O$ | 2 μL |

The reaction condition for enzymatic cleavage comprises: incubation at 37° C. for 1 hr.

After enzymatic cleavage, the enzymatically cleaved product is purified through the following process.

Anhydrous ethanol that is 2-3 times the volume of the enzymatically cleaved product and pre-frozen at −80° C. is added to the enzymatically cleaved product, stood at −20° C. for 20 min, and centrifuged at 4° C. for 10 min. The supernatant is removed, and the ethanol is air dried (for 5-8 min). 12 μL of TE Buffer (elution buffer) is added, and stood for 8 min. The concentration of MT-CD36-EGFP and the eukaryotic vector pLV4/StripII-HIS 10 is determined respectively and then stored at −20° C. until use.

Next, the purified enzymatically cleaved products of MT-CD36-EGFP and the eukaryotic vector pLV4/StripII-HIS10 are ligated by using the T4 DNA Ligase Kit (Promega), to obtain the pLV4/StripII-HIS10 expression vector (MT-CD36-EGFP-pLV4/StripII-HIS10) comprising the target fragment of the mutant CD36 gene and the EGFP fluorescent gene. The reaction system for ligation comprises:

| MT-CD36-EGFP: eukaryotic vectorpLV4/StripII-HIS10 molar ratio 7:1 (total volume: 1-8 μL) | |
|---|---|
| T4 DAN ligase 10 × Buffer | 1 μL |
| T4 DAN ligase | 1 μL |
| $H_2O$ q.s. to 10 μL. | |

Reaction condition for ligation comprises: incubation overnight at 4° C.

Finally, the ligated product is transformed into DH5a Chemically Competent Cells (Beijing TransGen Biotech, Inc). Positive clones are picked up from the *E. coli* DH5α cell line, cultured, multiplied, and confirmed, to obtain a successfully constructed MT-CD36-EGFP-pLV4/StripII-HIS10 eukaryotic expression vector. The process is specifically as follows.

The DH5α Chemically Competent Cells (Beijing TransGen Biotech, Inc) are removed from a freezer at −80° C., and thawed by standing on ice for 5 min. 50 μL of the DH5a Chemically Competent Cells is added to 10 μL of the ligated product obtained in the previous step, stood in an ice bath for 30 min, heat shocked at 42° C. for 1 min, and then stood in an ice bath for 2 min. 1 mL of the SOC medium is then added, and shaken for 1 hr on a shaker at 180 rpm. 300 μL of the bacterial suspension is aspirated and inoculated in a plate (a plate with LB medium to which Ampicillin (Amp, final concentration: 100 μg/mL) is added). The plate is transferred to an incubator and incubated overnight at 37° C. The single colony is picked up from the plate with well-grown transformants and transferred to a 1.5 mL centrifuge tube (to which 1 mL of Amp-containing SOC medium is added). The bamboo sticks for picking up the bacteria are correspondingly transferred one by one to 0.2 mL centrifuge tubes (to which 12 μL sterilized dd$H_2O$ is added), and labeled. The 1.5 mL centrifuge tube containing the bacterial suspension is shaken for 7-8 hrs on a shaker at 37° C.

During the culture and multiplication process, the bacterial suspension in the 0.2 mL centrifuge tube is lyzed by incubating for 20 min at 100° C., and then colony PCR is carried out using the 2×Taq Master Mix Kit (Vazyme). The reaction system for colony PCR comprises:

| | |
|---|---|
| $H_2O$ | 0.5 μL |
| 2 × Taq Master Mix | 12.5 μL |
| upstream primer CD36-F2 (10 μM) | 1 μL |
| downstream primer EGFP-R2 (10 μM) | 1 μL |
| bacterial suspension | 10 μL. |

The cycling parameters comprise:

| | |
|---|---|
| 98° C. | 5 min |
| 33 amplification cycles of: | |
| 98° C. | 10 sec |
| 56° C. | 30 sec |
| 72° C. | 90 sec; and |
| extension and storage at: | |
| 72° C. | 10 min |
| 12° C. | ∞. |

Selected the multiplied and culture colony that had be confirm having target band by colony PCR, and a part is aspirated for validation by sequencing, and the remaining is preserved for later use. 100-200 μL of the bacterial suspension transformed with the clone that is confirmed to be proper by sequencing is added to 16 mL LB medium, and shaken overnight on a shaker at 37° C. The plasmid is extracted by using an endotoxin-free Plasmid mini Preparation Kit (Tiangen Biotech Co, Ltd.). 5 μL of the extracted plasmid is subjected to 1.5% agarose gel electrophoresis, to observe that the size of the band is proper. The remaining plasmid is stored at −20° C. for later use.

4. The experimental method described in step (4) comprises the following.

Lentiviral packaging by using the Lenti-Pac™ HIV Expression packaging Kit (GeneCopoeia): $2\times10^8$ cells of the 293-T cell line in logarithmic growth phase are passaged and inoculated into a 25 mL culture flask, cultured for 24 hrs, and transfected when the cells reach 70%-80% confluence. 2 hrs before transfection, the cell culture medium is changed to Opti-MEM® I medium (GIBCO). 200 μL of a lentiviral packaging plasmid mix is formulated (in a sterilized 1.5 mL centrifuge tube, where 5 μg of the lentiviral recombinant expression plasmid MT-CD36-EGFP-pLV4/StripII-HIS10 constructed in step (3) and 5 μL of the LentiPac HIV reagent are added, and diluted with Opti-MEM® I medium to a final volume of 200 μL). 200 μL of a solution containing Endo-Fectin transfection reagent is formulated in another sterilized 1.5 mL centrifuge tube by adding 185 μL Opti-MEM® I medium and 15 μL EndoFectin transfection reagent. The formulated solution of the EndoFectin transfection reagent is slowly added dropwise to the lentiviral packaging plasmid mix with gently shaking to mix them uniformly. Then, the solution is incubated for 10-25 min at room temperature, to produce a DNA-EndoFectin mix. The DNA-EndoFectin mix is transferred to a culture of 293T cells, mixed uniformly, and incubated for 8 hrs in a cell incubator at 5% $CO_2$ and 37° C. The medium containing the transfection mix was removed, and 5 mL of DMEM medium containing 10% fetal bovine serum is added to each flask of cells. 10 μL of TiterBoost reagent is further added, and the culture flask is gently shaken, to mix the medium and the reagent uniformly, and then incubated in a cell incubator at 37° C. and 5% $CO_2$.

Harvest of the virus suspension: The culture supernatants of 293T cells are collected at 48 hours and 72 hours after transfection (after the virus suspension is collected at 48 hrs, 5 mL of DMEM medium containing 10% fetal bovine serum and 10 μL of TiterBoost reagent are added to the culture flask), and centrifuged at 4000 g for 10 min at 4° C. to remove cell debris. The supernatant is filtered through a 0.45 μM filter into a 15 mL centrifuge tube, biologically measured for the virus titer and stored at −80° C. until use.

Establishment of a CHO-K1 cell line (MT-CD36-CHO-K1 line) stably expressing the mutant CD36 gene by virus-mediated transfection: $4\times10^7$ CHO-K1 cells in logarithmic growth phase are inoculated into a 25 mL culture flask, added with DMEM medium containing 10% fetal bovine serum and 1% penicillin—streptomycin solution, and cultured for 24 hrs. The medium is removed when the cells reach 80%-90% confluence, and 4 mL of DMEM medium (containing 10% heat-inactivated fetal bovine serum and 1% penicillin—streptomycin solution) and 100 μL of the viral suspension (with a virus titer of $2\times10^5$ TU/mL) are added, and cultured overnight at 5% $CO_2$ and 37° C. The medium was removed, and the cells are screened by using 5 mL of DMEM medium containing 0.2 μg/mL puromycin (Sigma) (containing 10% heat-inactivated fetal bovine serum and 1% penicillin—streptomycin solution). At this time, cells successfully transfected with lentiviral packaging plasmid show green fluorescence under a fluorescence microscope, while cells that are not successfully transfected show no fluorescence. After screening by adding medium containing puromycin, the state of cells is observed every 24 hours. The medium containing puromycin is replaced every 48 hours and the culture is continued for at least one month.

Verification of the established MT-CD36-CHO-K1 line: The MT-CD36-CHO-K1 line in logarithmic growth phase is collected, and RNA is extracted and amplified by RT-PCR following the method as described in step (1), to obtain a cDNA fragment of mutant CD36 gene. The cDNA fragment is sequenced, and the sequencing result is in agreement with that in step (1), suggesting that the established MT-CD36-CHO-K1 line can accurately express the mutant CD36 gene at a molecular level. The CD36 expression on the cell surface of the MT-CD36-CHO-K1 line is confirmed by flow cytometry, and the expression of the CD36 protein by MT-CD36-CHO-K1 line is confirmed by western-blotting.

5. In step (5), the processes for establishing the positive control Normal-CD36-CHO-K1 line stably expressing normal CD36 and the negative control EGFP-pLV4-CHO-K1 line stably expressing the EGFP fluorescent protein alone are as follows.

In the disclosure, total RNA is extracted from a whole blood sample derived from a CD36 expression-positive individual, and following the process in steps (1)-(4), a Normal-CD36-CHO-K1 line stably expressing normal CD36 gene is established as a positive control in an experiment. The cell line is positive in CD36 expression, and in a western-blotting experiment, the expressed CD36-EGFP fusion protein appears as two CD36 positive bands at about 115000D on the western blot, which may be attributed to different protein conformations.

A EGFP-pLV4-CHO-K1 line having EGFP fluorescent gene-containing plasmid transformed therein and stably expressing the EGFP fluorescent protein alone is established as a negative control. The experimental method is as follows.

A target EGFP gene fragment comprising an EcoR 1 cleavage site and protective bases, the full-length gene sequence of the EGFP fluorescent reporter gene, and a XhoI cleavage site and protective bases is obtained by amplification using a forward and reverse primer, in which the forward primer EGFP-F3 has a sequence of 5'-CCGGAATTCATGGTGAGCAAGGGCGAGGA-3' (SEQ. ID. NO. 7), and the reverse primer is the downstream primer EGFP-R2 (SEQ. ID. NO. 6) used in amplification of the gene fragment of MT-CD36-EGFP-2 in step (2). The length of the amplified target fragment is 743 bp. The upstream primer EGFP-F3 comprises a EcoR1 cleavage site and protective bases at the 5' end. The amplification region covers the EcoR1 cleavage site and protective bases, the full-length fragment of the EGFP CDS, and the XhoI cleavage site and protective bases.

PCR amplification is carried out by using the eukaryotic plasmid pEGFP-N1 containing the EGFP fluorescent reporter gene (manufactured by Suzhou Genepharma Co., Ltd) as a template and using the EGFP-F3 and EGFP-R2 as a forward and reverse primer, to obtain the target EGFP gene fragment. The reaction system has a composition of (the total volume of the reaction system is 25 μL):

| | |
|---|---|
| *dd*$H_2O$ | 16 μL |
| 5 × SF Buffer (with 10 mM MgCl2) (Vazyme) | 5 μL |
| dNTP mix (10 mM each) | 0.5 μL |
| EGFP-F3 (10 μM) | 0.5 μL |
| EGFP-R2 (10 μM) | 0.5 μL |
| pEGFP-N1 plasmid | 1 μL |
| DMSO | 1 μL |
| HS suffer-Fieviy DNA polymerase (Vazyme) | 0.5 μL |

The cycling parameters for PCR amplification are the same as those for amplification of MT-CD36-EGFP-1 and MT-CD36-EGFP-2 in step (2).

The amplified EGFP gene product is subjected to 1.5% agarose gel electrophoresis (105 v, 40 min), gel cutting, and gel extraction by using the AxyPrep DNA Gel Extraction Kit (AXYGEN). The extracted product is sequenced, to confirm that the amplified product is consistent in sequence with the target fragment. Following the processes insteps (3) and (4), a eukaryotic expression vector for expressing the EGFP gene is constructed, and an EGFP-pLV4-CHO-K1 line stably expressing the EGFP fluorescent protein alone is established.

Critical Features and Contributions of the Method According to the Present Disclosure The disclosure is based on a thorough understanding of CD36 genetics and the important role of CD36 on human in physiology, pathology, functions and clinical medicines, and recognizes that the mutant CD36 gene is a key factor critical to CD36 research and application. A method for establishing a eukaryotic cell line stably expressing mutant CD36 gene is developed and the method is also applicable to the establishment of a eukaryotic cell line stably expressing normal CD36 gene.

In the method of the disclosure, a target gene fragment for ligation during the construction of a eukaryotic vector expressing the mutant CD36 gene is prepared by using two primers for RT-PCR of mRNA and four primers for SOE-PCR, exploring the optimal annealing temperature and adjusting the conditions comprising $Mg^{2+}$ concentration and primer concentration; the eukaryotic vector expressing the mutant CD36 gene is constructed by exploring the optimal enzymatic cleavage conditions in the construction of the eukaryotic vector expressing the mutant CD36 gene and the reaction conditions for ligating a insert fragment to the eukaryotic vector; and the purpose of establishing a eukaryotic cell line stably expressing the mutant CD36 gene that encodes CD36 deficiency is achieved by exploring the viral packaging, transfection, and screening conditions for establishing the eukaryotic cell line stably expressing the mutant CD36 gene by virus-mediated transfection. Because the integrity of the gene fragment of the CD36 open reading frame and the expression of the EGFP fluorescent gene are fully taken into account when designing the primers, the integrity of the target CD36 gene fragment and the EGFP fluorescent gene ligated is ensured, and the ligated EGFP fluorescent gene allows the observation of cells screened under a fluorescence microscope during the screening process in the subsequent establishment of the eukaryotic cell lines stably expressing the mutant CD36 gene during screening. During the establishment of the eukaryotic stable expression cell line of CD36 mutant gene that encodes CD36 deficiency, in the steps of RT-PCR, SOE-PCR, and constructing the MT-CD36-EGFP-pLV4/StripII-HIS10 eukaryotic expression vector, gene sequencing is employed to ensure the accuracy of the sequence of the target fragments in each step. Expression of the ligated target MT-CD36 gene in the established eukaryotic CHO-K1 cell line (MT-CD36-CHO-K1 line) stably expressing the mutant CD36 gene is confirmed at a molecular level by extracting RNA from the eukaryotic expression cell line, reverse transcribing, and sequencing. The variation in CD36 protein expression caused by the MT-CD36 gene is confirmed by flow cytometry and western-blotting. This method is not only applicable to the establishment of a eukaryotic cell line stably expressing the CD36 gene with mutations leading to CD36 deficiency such as single nucleotide substitution, base insertion, and base deletion, etc (where the mutation point cannot be located in a 18-base sequence in the 5' to 3' direction starting from the protein expression promoter ATG and the 3' to 5' direction starting from the stop codon) and is also applicable to the establishment of a CD36-positive eukaryotic cell line stably expressing normal CD36 gene.

Briefly, the establishment method contributes mainly in the following aspects.

1. The developed method for establishing eukaryotic stable expression cell line of CD36 mutant gene that encodes CD36 deficiency is also applicable to the establishment of eukaryotic stable expression cell line of normal CD36 gene that encodes normal CD36.

2. The problems of permanent and stable preservation and preparation of various CD36 mutant genes and expressed proteins are solved. An infinitely valuable genetic resources basis is provided for studying the molecular structure, expression, regulation and functions of CD36, elucidating the mechanism of action of CD36 in various physiological and pathological processes in human and further for deep insight into the important role of CD36 in clinical treatment.

3. A high-quality work platform is provided for development of drugs and screening of drug target in the treatment of CD36-related hemostasis, thrombosis, alloimmune platelet disease, hypercholesterolemia, obesity, peripheral atherosclerosis, arterial hypertension, cardiomyopathy, diabetes, malaria, presenile dementia (Alzheimer's disease) and other diseases.

4. The established cell line can be directly used as a panel cell for detecting anti-CD36 antibodies causing platelet transfusion refractoriness to ensure the safety and efficacy of platelet transfusion therapy.

the 220T-CD36-CHO-K1 line is negative in CD36 protein expression; (2): the negative control EGFP-pLV4-CHO-K1 line is negative in CD36 protein expression; (3) the blank control CHO-K1 line is negative in CD36 protein expression; and (4): the positive control NORMAL-CD36-CHO-K1 line is positive in CD36 protein expression.

DETAILED DESCRIPTION OF THE EMBODIMENTS

The following examples are further explanations and illustrations of the disclosure, and not intended to limit the disclosure in any way.

On the basis of molecular genetics leading to CD36 deficiency, the disclosure provides a method for establishing eukaryotic stable expression cell line of CD36 mutant gene that encodes human CD36 deficiency. The method for establishing eukaryotic stable expression cell line of CD36 mutant gene that encodes CD36 deficiency can be established by designing primers for RT-PCR of mutant CD36 gene and primers for construction of a eukaryotic vector, exploring the optimal annealing temperature and adjusting the conditions comprising $Mg^{2+}$ concentration and primer concentration, exploring the optimal enzymatic cleavage conditions in the construction of the eukaryotic vector for the mutant CD36 gene and the reaction conditions for ligating a insert fragment to the eukaryotic vector, and exploring the viral packaging, transfection, and screening conditions for establishing the eukaryotic cell line stably expressing the mutant CD36 gene by virus-mediated transfection.

Example 1

In this example, an implementation for establishing a eukaryotic cell line, "220T-CD36-CHO-K1 line" stably expressing the mutant CD36 gene 220C>T (Gln74stop) (GenBank Accession No.: KF539919.1) encoding CD36 deficiency by the method for establishing eukaryotic stable expression cell line of CD36 mutant gene that encodes CD36 deficiency according to the disclosure is specifically described.

Figure 1:
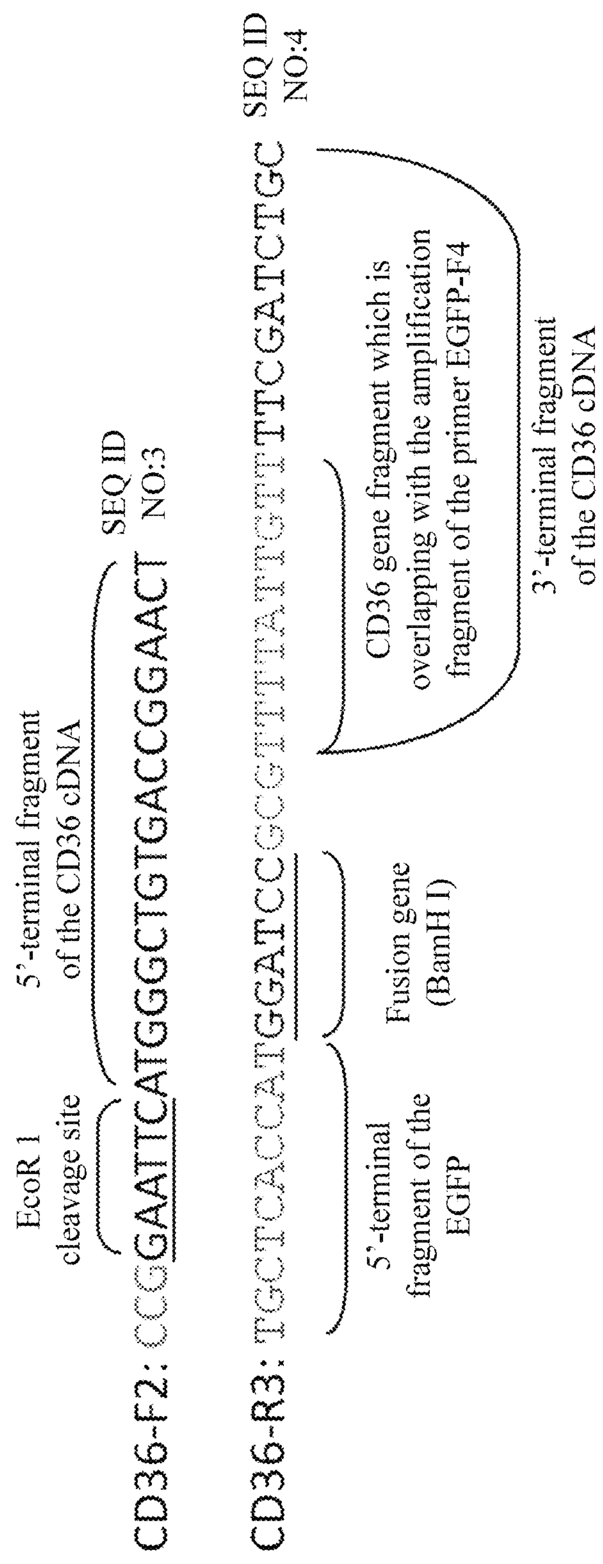
FIG. 1 is a schematic view showing the primers for amplification of a target fragment of CD36-EGFP-1 by SOE-PCR.
Figure 2:
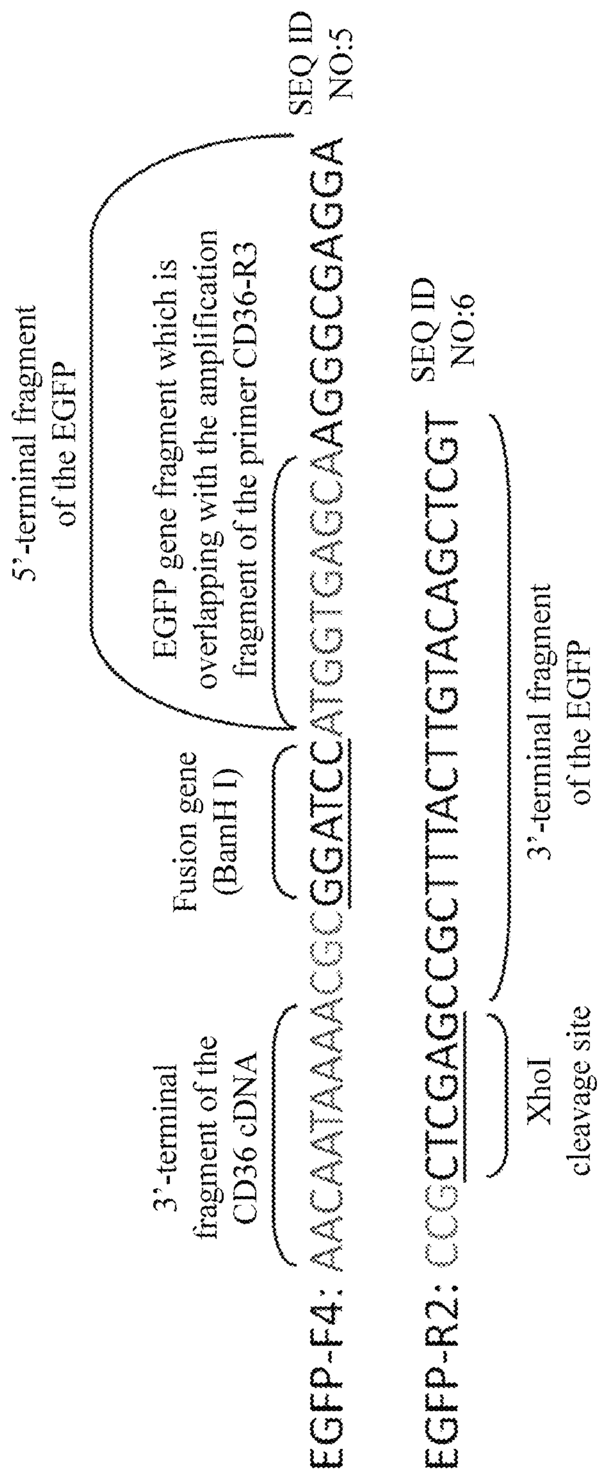
FIG. 2 is a schematic view showing the primers for amplification of a target fragment of CD36-EGFP-2 by SOE-PCR.
Figure 3:
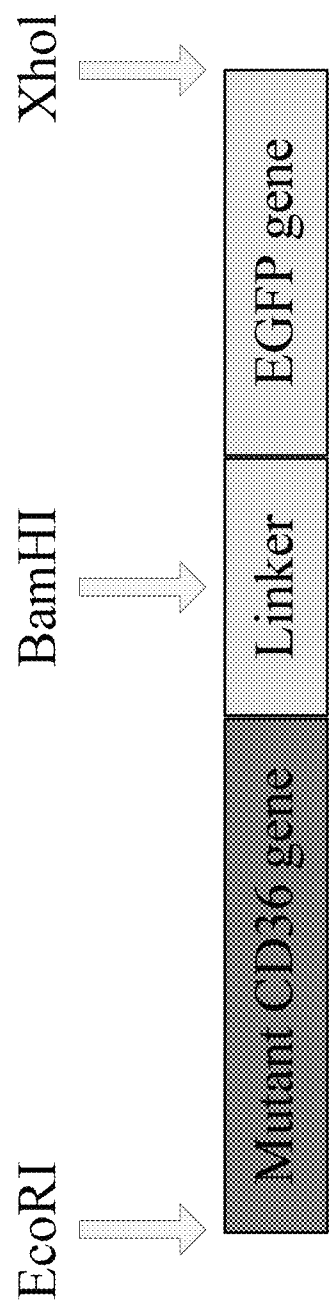
FIG. 3 is a schematic view showing the final target fragment of MT-CD36-EGFP amplified by SOE-PCR.
Figure 4:
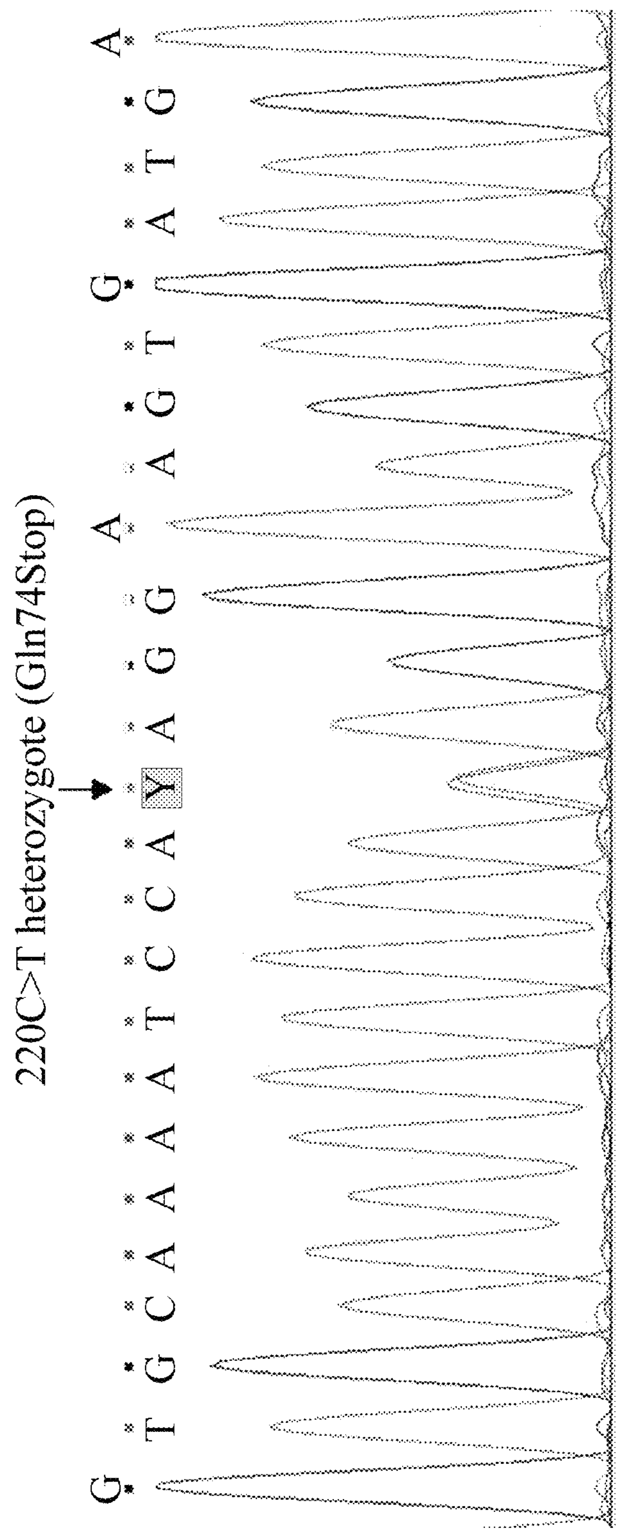
FIG. 4 shows a sequencing chromatogram of SEQ ID NO: 8 which is a portion of the sequence of the CD36 gene in a CD36-deficient individual ZYT in Example 1, showing that the exon-4 has C220T mutation.

A CD36-deficient individual that was confirmed to have mutation of C220T by exon sequencing of the CD36 gene (where the individual was designated as ZYT, and the exon sequencing results were shown in FIG. 4) was chosen. 5 mL of venous blood was drawn from the individual with informed consent, EDTA was added for anti-coagulation, and total RNA was extracted from the blood sample. A target fragment of CD36 cDNA (ZYT-CD36 cDNA) was amplified by RT-PCR using the first pair of PCR primers of the disclosure comprising an upstream primer YC-36F and a downstream primer YC-36R, and using the TaKaRa One step RNA PCR Kit (AMV). The amplification was carried out in ABI 9700PCR machine, and the reaction system for PCR amplification comprised:

| | |
|---|---|
| 10 × one step RNA PCR Buffer | 5 μL |
| 25 mM MgCl2 | 10 μL |
| 10 mM dNTPs | 5 μL |
| Rnase Inhibitor (40 u/μL) | 1 μL |
| AMV Rtase XL | 1 μL |
| AMV-Optimized Taq | 1 μL |
| Primer YC-36F (20 μM) | 1 μL |
| Primer YC-36R (20 μM) | 1 μL |
| RNA (100-500 ng/μL) | 10 μL |
| $H_2O$ | 15 μL |

The cycling parameters comprised:

| | |
|---|---|
| 50° C. | 30 min |
| 94° C. | 2 min |
| 30 amplification cycles of: | |
| 94° C. | 30 sec |
| 60° C. | 30 sec |
| 72° C. | 2 min; and |
| extension and storage at: | |
| 72° C. | 10 min |
| 12° C. | ∞. |

Figure 5:
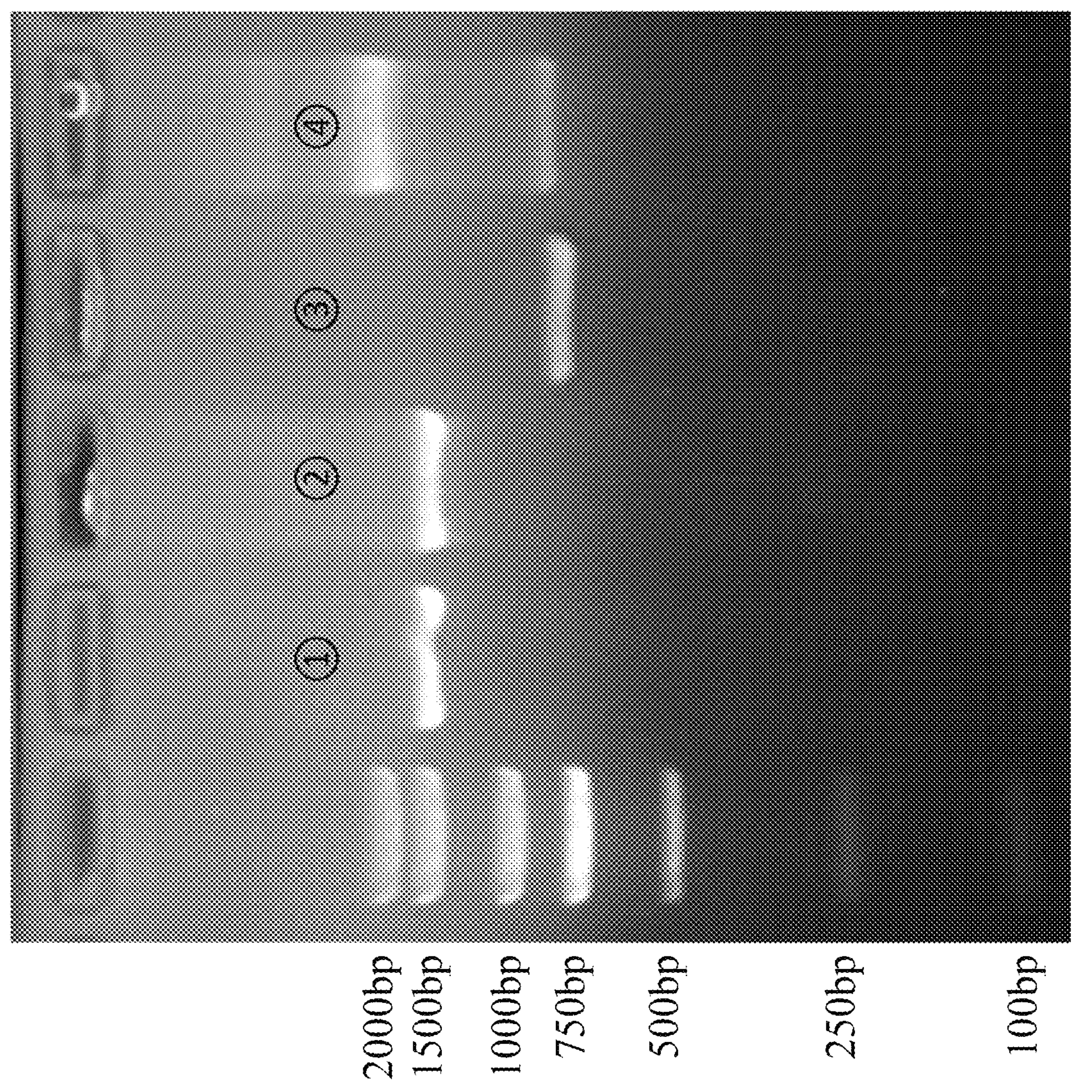
FIG. 5 shows amplification of the CD36 cDNA from the CD36-deficient individual ZYT (1), the target fragments of ZYT-CD36-EGFP-1 (2) and ZYT-CD36-EGFP-2 (3), and the product ZYT-CD36-EGFP (4) ligated by SOE-PCR in Example 1.
Figure 6:
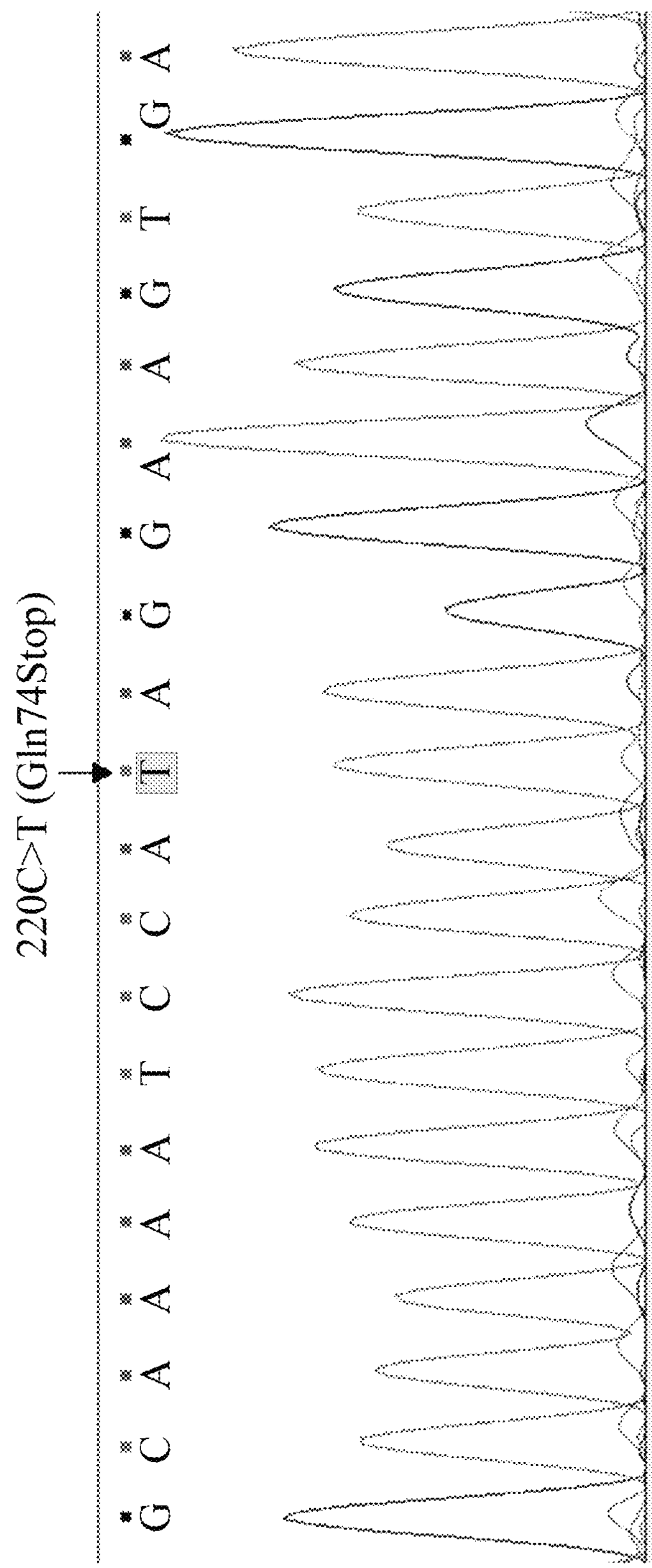
FIG. 6 shows a sequencing chromatogram of SEQ ID NO: 9 which is a portion of the cDNA sequence of the CD36 gene in a CD36-deficient individual ZYT in Example 1, showing 220C>T (Gln74Stop) mutation.

5 μL of the PCR product was stained by DNA green fluorescent dye (Beijing Tiandz Gene Technology Co., Ltd), and subjected to 1.5% agarose gel electrophoresis. With DL2000 Plus DNA Marker from Vazyme as a control, a band of specific PCR product was observed in a gel imaging system. The band of the PCR product was clear and specific, as shown in FIG. 5(1). 5 μL of the PCR product was sequenced, and the sequencing results were shown in FIG. 6. The remaining PCR product was stored at −80° C. until use.

Next, a target gene fragment of ZYT-CD36-EGFP-1 comprising an EcoR 1 cleavage site and protective bases, a full-length gene sequence of the CD36 protein coding region, a fusion gene BamH I and protective bases, and a portion of the 5'-terminal sequence of the EGFP fluorescent reporter gene was obtained by amplification using the second pair of PCR primers of the present invention comprising an upstream primer CD36-F2 and a downstream primer CD36-R3 and using ZYT-CD36 cDNA as a DNA template. The amplification was carried out in ABI 9700 PCR machine, and the reaction system for PCR amplification comprised a composition of:

| | |
|---|---|
| *dd*$H_2O$ | 15 μL |
| 5 × SF Buffer (with 10 mM MgCl2) (Vazyme) | 5 μL |
| dNTP mix (10 mM each) | 0.5 μL |
| CD36-F2 (10 μM) | 1 μL |
| CD36-R3 (10 μM) | 1 μL |
| ZYT-CD36 cDNA | 1 μL |
| DMSO | 1 μL |
| HS suffer-Fieviy DNA polymerase (Vazyme) | 0.5 μL |

The cycling parameters comprised:

| | |
|---|---|
| 96° C. | 5 min |
| 33 amplification cycles of: | |
| 96° C. | 30 sec |
| 60° C. | 30 sec |
| 72° C. | 90 sec; and |
| extension and storage at: | |
| 72° C. | 10 min |
| 12° C. | ∞. |

5 μL of the PCR product was stained by DNA green fluorescent dye (Beijing Tiandz Gene Technology Co., Ltd), and subjected to 1.5% agarose gel electrophoresis. With DL2000 Plus DNA Marker from Vazyme as a control, a band of specific PCR product was observed in a gel imaging system. The band of the PCR product was clear and specific, as shown in FIG. 5(2). The remaining PCR product was stored at −80° C. until use.

A target gene fragment of ZYT-CD36-EGFP-2 comprising a portion of the 3'-terminal fragment of the CD36 encoding cDNA region, a fusion gene BamH I and protective bases, the full-length gene sequence of the EGFP fluorescent reporter gene, and a XhoI cleavage site and protective bases was obtained by amplification using the third pair of PCR primers of the disclosure comprising an upstream primer EGFP-F4 and a downstream primer EGFP-R2 and using the eukaryotic plasmid pEGFP-N1 containing the EGFP fluorescent reporter gene (manufactured by Suzhou Genepharma Co., Ltd) as a template. The amplification was carried out in ABI 9700 PCR machine, and the reaction system for PCR amplification comprised a composition of:

| | |
|---|---|
| $ddH_2O$ | 16 μL |
| 5 × SF Buffer (with 10 mM MgCl2) (Vazyme) | 5 μL |
| dNTP mix (10 mM each) | 0.5 μL |
| EGFP-F4 (10 μM) | 0.5 μL |
| EGFP-R2 (10 μM) | 0.5 μL |
| pEGFP-N1 plasmid | 1 μL |
| DMSO | 1 μL |
| HS suffer-Fieviy DNA polymerase (Vazyme) | 0.5 μL |

The cycling parameters comprised:

| | |
|---|---|
| 96° C. | 5 min |
| 33 amplification cycles of: | |
| 96° C. | 30 sec |
| 60° C. | 30 sec |
| 72° C. | 90 sec; and |
| extension and storage at: | |
| 72° C. | 10 min |
| 12° C. | ∞ |

5 μL of the PCR product was stained by DNA green fluorescent dye (Beijing Tiandz Gene Technology Co., Ltd), and subjected to 1.5% agarose gel electrophoresis.

With DL2000 Plus DNAMarker from Vazyme as a control, a band of specific PCR product was observed in a gel imaging system. The band of the PCR product was clear and specific, as shown in FIG. 5(3). The remaining PCR product was stored at −80° C. until use.

A gene fragment of ZYT-CD36-EGFP comprising the full-length cDNA encoding region of the mutant CD36 gene ZYT, a fusion gene BamH I and protective bases, the full-length EGFP fluorescent gene, and desired EcoR1 and XhoI cleavage site was obtained by splicing and amplication by SOE-PCR using the upstream primer CD36-F2 in the second pair of primers and the downstream primer EGFP-R2 in the third pair of primers of the disclosure, and using ZYT-CD36-EGFP-1 and ZYT-CD36-EGFP-2 as templates. The amplification was carried out in ABI 9700 PCR machine, and the reaction system for PCR amplification comprised a composition of:

| | |
|---|---|
| $H_2O$ | 24 μL |
| 5 × SF Buffer (with 10 mM MgCl2) (phanta ™) | 10 μL |
| dNTP Mix (10 mM each) | 1 μL |
| ZYT-CD36-EGFP-1 | 4 μL |
| ZYT-CD36-EGFP-2 | 4 μL |
| phanta ™HS Suffer-Fideliy DNA Polymerase | 1 μL |

The cycling parameters comprised:

| | |
|---|---|
| 98° C. | 5 min |
| 15 amplification cycles of: | |
| 98° C. | 5 min |
| 72° C. | 1 min. |

A system having the following composition was added to the reaction tube after the reaction was completed:

| | |
|---|---|
| CD36-F2 | 2 μL |
| EGFP-R2 | 2 μL |
| DMSO | 2 μL. |

Amplification is continued through a process which is performed under the following cycling parameters:

| | |
|---|---|
| 20 amplification cycles of: | |
| 98° C. | 10 sec |
| 56° C. | 30 sec |
| 72° C. | 60 sec; and |
| extension and storage at: | |
| 72° C. | 10 min |
| 12° C. | ∞. |

5 μL of the PCR product was stained by DNA green fluorescent dye (Beijing Tiandz Gene Technology Co., Ltd), and subjected to 1.5% agarose gel electrophoresis. With DL2000 Plus DNAMarker from Vazyme as a control, a band of specific PCR product was observed in a gel imaging system. The band of the PCR product was clear and specific, as shown in FIG. 5(4). The target fragment of 2165 bp was taken by gel cutting, and subjected to gel extraction by using the AxyPrep DNA Gel Extraction Kit (AXYGEN). 4 μL of the extracted product was sequenced, to confirm that the amplified product is consistent in sequence with the target fragment. Then, the remaining extracted product was stored at −80° C. until use.

After the purified target fragment of ZYT-CD36-EGFP was obtained, ZYT-CD36-EGFP and the eukaryotic vector pLV4/StripII-HIS10 (Shenzhen Angran Biotechnology Co., Ltd.) were enzymatically cleaved by using the EcoR1/XhoI DNA Endonuclease Kit (Beyotime Biotechnology). The reaction system comprised:

| | |
|---|---|
| ZYT-CD36-EGFP or eukaryotic vector pLV4/StripII-HIS10 | 14 μL |
| 10 × Buffer Y | 2 μL |
| ECOR 1 | 1 μL |
| Xhol | 1 μL |
| $ddH_2O$ | 2 μL |

The reaction condition for enzymatic cleavage comprised: incubation at 37° C. for 1 hr.

After enzymatic cleavage, the enzymatically cleaved product was purified through the following process.

Anhydrous ethanol that was 2-3 times the volume of the enzymatically cleaved product and pre-frozen at −80° C. was added to the enzymatically cleaved product, stood at −20° C. for 20 min, and centrifuged at 4° C. for 10 min. The supernatant was removed and, and the ethanol was air dried (for 5-8 min). 12 μL of TE Buffer (elution buffer) was added, and stood for 8 min. The concentration of MT-CD36-EGFP and the eukaryotic vector pLV4/StripII-HIS10 was determined respectively and then stored at −20° C. for later use.

The purified enzymatically cleaved products of MT-CD36-EGFP and the eukaryotic vector pLV4/StripII-HIS10 were ligated by using the T4 DNA Ligase Kit (Promega), to obtain a pLV4/StripII-HIS10 expression vector (C220T-CD36-EGFP-pLV4/StripII-HIS10) comprising the target fragment of the mutant CD36 gene and the EGFP fluorescent gene. The reaction system for ligation comprised:

| ZYT-CD36-EGFP: eukaryotic vectorpLV4/StripII-HIS10 molar ratio 7:1 (total volume: 1-8 μL) | |
|---|---|
| T4 DAN ligase 10 × Buffer | 1 μL |
| T4 DAN ligase | 1 μL |
| $H_2O$ q.s. to 10 μL. | |

Reaction condition for ligation comprised: incubation overnight at 4° C.

The ligated product was transformed into DH5α Chemically Competent Cells (Beijing TransGen Biotech, Inc). Positive clones were picked up from the *E. coli* DH5α cell line, cultured, multiplied, and confirmed, to obtain a successfully constructed 220T-CD36-EGFP-pLV4/StripII-HIS10eukaryotic expression vector. The process was specifically as follows.

The DH5α Chemically Competent Cells (Beijing TransGen Biotech, Inc) were removed from a freezer at −80° C., and thawed by standing on ice for 5 min. 50 μL of the DH5α Chemically Competent Cells was aspirated to 10 μL of the ligated product obtained in the previous step (1 μL of a solution III was added to the ligated product before transformation), stood in an ice bath for 30 min, heat shocked at 42° C. for 1 min, and then stood in an ice bath for 2 min. 1 mL of the SOC medium was then added, and shaken for 1 hr on a shaker at 180 rpm. 300 μL of the bacterial suspension was aspirated and inoculated in a plate (a plate with LB medium to which Ampicillin (Amp, final concentration: 100 μg/mL) was added). The plate was transferred to an incubator and incubated overnight at 37° C. A single colony was picked up from the plate with well-grown transformants and transferred to a 1.5 mL centrifuge tube (to which 1 mL of Amp-containing SOC medium was added). The bamboo sticks for picking up the bacteria were correspondingly transferred one by one to 0.2 mL centrifuge tubes (to which 12 μL sterilized $ddH_2O$ was added), and labeled. The 1.5 mL centrifuge tube containing the bacterial suspension was shaken for 7-8 hrs on a shaker at 37° C.

During the culture and multiplication process, colony PCR amplification was carried out by using the 2×Taq Master Mix Kit (Vazyme) using the upstream primer CD36-F2 in the second pair of primers and the downstream primer EGFP-R2 in the third pair of primers of the present disclosure and using the bacterial suspension in the 0.2 mL centrifuge tube (which was lyzed by incubating for 20 min at 100° C. before PCR amplification) as a template. The amplification was carried out in ABI 9700 PCR machine, and the reaction system for PCR amplification comprised a composition of:

| | |
|---|---|
| $H_2O$ | 0.5 μL |
| 2 × Taq Master Mix | 12.5 μL |
| upstream primer CD36-F2 (10 μM) | 1 μL |
| downstream primer EGFP-R2 (10 μM) | 1 μL |
| bacterial suspension | 10 μL |

The cycling parameters comprised:

| | |
|---|---|
| 98° C. | 5 min |
| 33 amplification cycles of: | |
| 98° C. | 10 sec |
| 56° C. | 30 sec |
| 72° C. | 90 sec; and |
| extension and storage at: | |
| 72° C. | 10 min |
| 12° C. | ∞. |

Figure 7:
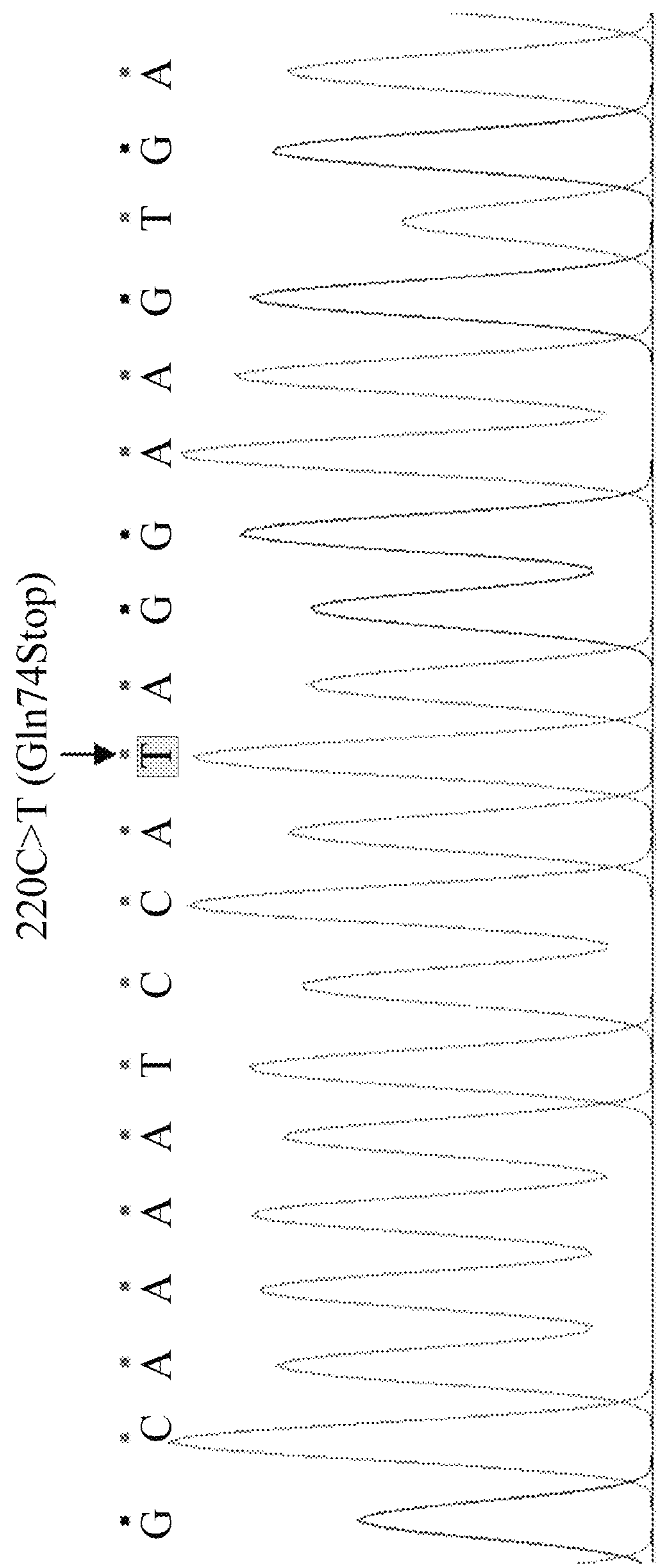
FIG. 7 shows a sequencing chromatogram of SEQ ID NO: 10 which is a portion of the sequence of the 220T-CD36-EGFP-pLV4/StripII-HIS10 eukaryotic expression vector successfully constructed in Example 1.

5 μL of the PCR product was stained by DNA green fluorescent dye (Beijing Tiandz Gene Technology Co., Ltd), and subjected to 1.5% agarose gel electrophoresis. With DL2000 Plus DNAMarker from Vazyme as a control, a band of specific PCR product was observed in a gel imaging system. The band of the PCR product of the picked colony was clear and specific, and the size of the fragment was in agreement with the size of the product ZYT-CD36-EGFP amplified by SOE-PCR. The corresponding colony was multiplied and cultured, and a part was aspirated for validation by sequencing and the remaining is preserved for later use. The result of confirmation by sequencing indicates CD36 220T (as shown in FIG. 7). 100-200 μL of the bacterial suspension transformed with a clone in which the remaining sequence is consistent with that in the ligated sequence of ZYT-CD36-EGFP was added to 16 mL LB medium, shaken overnight on a shaker at 37° C., multiplied and cultured to obtain a successfully constructed 220T-CD36-EGFP-pLV4/StripII-HIS10 eukaryotic expression vector. The plasmid was extracted by using an endotoxin-free Plasmid mini Preparation Kit (Tiangen Biotech Co, Ltd.). 5 μL of the extracted plasmid was subjected to 1.5% agarose gel electrophoresis, to observe that the size of the band is proper. The remaining plasmid was stored at −20° C. for later use.

Finally, the 220T-CD36-EGFP-pLV4/StripII-HIS10 eukaryotic expression vector was transfected into the CHO-K1 cell line by using virus-mediated transfection of eukaryotic cells, and screened to construct a eukaryotic cell line (220T-CD36-CHO-K1) stably expressing the mutant CD36 220C>T gene encoding CD36 deficiency. The process was specifically as follows.

Lentiviral packaging by using the Lenti-Pac™ HIV Expression packaging Kit (GeneCopoeia): $2\times10^8$ cells of the 293-T cell line in logarithmic growth phase were passaged and inoculated into a 25 mL cell culture flask, cultured for 24 hrs, and transfected when the cells reached 70%-80% confluence. 2 hrs before transfection, the cell culture medium was changed to Opti-MEM® I medium (GIBCO). 200 μL of a lentiviral packaging plasmid mix was formulated (in a sterilized 1.5 mL centrifuge tube, where 5 μg of the eukaryotic expression plasmid 220T-CD36-EGFP-pLV4/StripII-HIS10 successfully constructed and 5 μL of the LentiPac HIV reagent were added, and diluted with Opti-MEM® I medium to a final volume of 200 μL). 200 μL of a solution containing EndoFectin transfection reagent was formulated in another sterilized 1.5 mL centrifuge tube by adding 185 μL Opti-MEM® I medium and 15 μL EndoFectin transfection reagent. The formulated solution of the EndoFectin transfection reagent was slowly added dropwise to the lentiviral packaging plasmid mix with gently shaking to mix them uniformly. Then, the solution was incubated for 10-25 min at room temperature, to produce a DNA-EndoFectin mix. The DNA-EndoFectin mix was transferred to a culture of 293T cells, mixed uniformly, and incubated for 8 hrs in a cell incubator at 5% $CO_2$ and 37° C. The medium containing the transfection mix was removed, and 5 mL of DMEM medium containing 10% fetal bovine serum was added to each flask of cells. 10 μL of TiterBoost reagent was further added, and the culture flask was gently shaken, to mix the medium and the reagent uniformly, and then incubated in a cell incubator at 37° C. and 5% $CO_2$.

Harvest of the virus suspension: The culture supernatants of 293T cells were collected 48 hours and 72 hours after transfection (after the virus suspension was collected at 48 hrs, 5 mL of DMEM medium containing 10% fetal bovine serum and 10 μL of TiterBoost reagent were added to the culture flask), and centrifuged at 4000 g for 10 min at 4° C. to remove cell debris. The supernatant was filtered through a 0.45 μM filter into a 15 mL centrifuge tube, biologically measured for the virus titer and stored at −80° C. until use.

Establishment of a eukaryotic cell line (220T-CD36-CHO-K1 line) stably expressing the mutant CD36 220C>T gene by transfecting the CHO-K1 cell line using the harvested virus suspension, and screening with puromycin: $4\times10^7$ CHO-K1 cells in logarithmic growth phase were inoculated into a 25 mL culture flask, added with DMEM medium containing 10% fetal bovine serum and 1% penicillin—streptomycin solution, and cultured for 24 hrs. The medium was removed when the cells reached 80%-90% confluence, and 4 mL of DMEM medium (containing 10% heat-inactivated fetal bovine serum and 1% penicillin—streptomycin solution) and 100 μL of the viral suspension (with a virus titer of $2\times10^5$ TU/mL) were added, and cultured overnight at 5% $CO_2$ and 37° C. The medium was removed, and the cells were screened by using 5 mL of DMEM medium containing 0.2 μg/mL puromycin (Sigma) (containing 10% heat-inactivated fetal bovine serum and 1% penicillin—streptomycin solution). The state of cells was observed every 24 hours. The medium containing puromycin was replaced every 48 hours and the culture was continued for at least one month.

A Normal-CD36-CHO-K1 line stably expressing normal CD36 and a EGFP-pLV4-CHO-K1 line having merely EGFP fluorescent gene-containing plasmid transformed therein and stably expressing the EGFP fluorescent protein alone were established as a positive control and a negative control respectively in experiment. The process was as follows.

Total RNA was extracted from a whole blood sample derived from a CD36 expression-positive individual, and following the process in the above steps, a Normal-CD36-CHO-K1 line stably expressing normal CD36 gene was established as a positive control in an experiment.

A EGFP-pLV4-CHO-K1 line having EGFP fluorescent gene-containing plasmid transformed therein and stably expressing the EGFP fluorescent protein alone was established as a negative control. The experimental method was as follows.

PCR amplification was carried out by using the eukaryotic plasmid pEGFP-N1 containing the EGFP fluorescent reporter gene (manufactured by Suzhou Genepharma Co., Ltd) as a template and using EGFP-F3 and EGFP-R2 as forward and reverse primer, to obtain a target EGFP gene fragment comprising an EcoR 1 cleavage site and protective bases, the full-length gene sequence of the EGFP fluorescent reporter gene, and a XhoI cleavage site and protective bases. The reaction system had a composition of (the total volume of the reaction system was 25 μL):

| | |
|---|---|
| $ddH_2O$ | 16 μL |
| 5 × SF Buffer (with 10 mM Mgcl2) (Vazyme) | 5 μL |
| dNTP mix (10 mM each) | 0.5 μL |
| EGFP-F3 (10 μM) | 0.5 μL |
| EGFP-R2 (10 μM) | 0.5 μL |
| pEGFP-N1 plasmid | 1 μL |
| DMSO | 1 μL |
| HS suffer-Fieviy DNA polymerase (Vazyme) | 0.5 μL |

The cycling parameters for PCR amplification were the same as those for amplification of the target fragments of ZYT-CD36-EGFP-1 and ZYT-CD36-EGFP-2 in the above steps.

The amplified EGFP gene product was subjected to 1.5% agarose gel electrophoresis (105 v, 40 min), gel cutting, and gel extraction by using the AxyPrep DNA Gel Extraction Kit (AXYGEN). The extracted product was sequenced, to confirm that the amplified product is consistent in sequence with the target fragment. Following the method for constructing the 220T-CD36-EGFP-pLV4/StripII-HIS10 plasmid and the method for establishing and screening the 220T-CD36-CHO-K1 cell line, a eukaryotic expression vector for expressing the EGFP gene was constructed, and an EGFP-pLV4-CHO-K1 line stably expressing the EGFP fluorescent protein alone was established.

Figure 8:
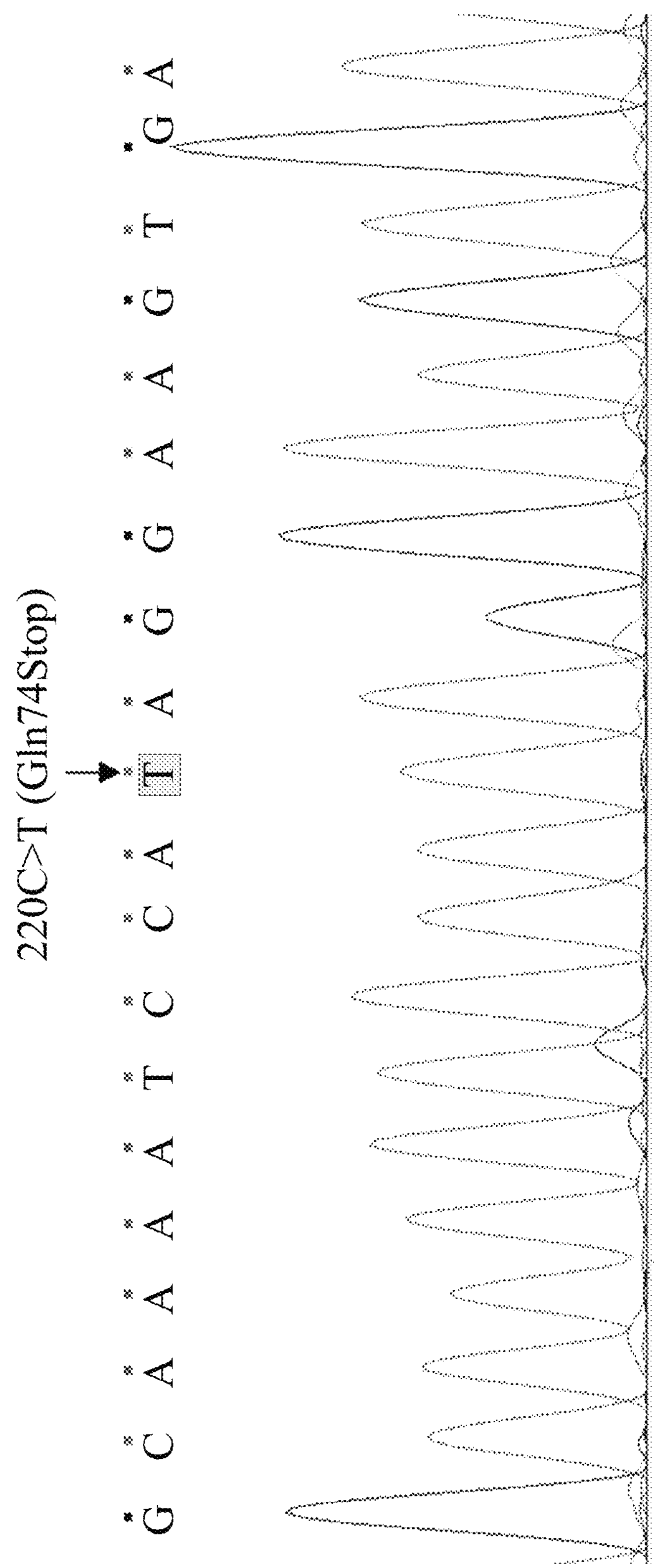
FIG. 8 shows a sequencing chromatogram of SEQ ID NO: 11 which is a portion of the cDNA sequence of the eukaryotic CHO-K1 cell line (220T-CD36-CHO-K1 line) stably expressing the mutant CD36 gene (220C>T) in Example 1.

Confirmation of the established 220T-CD36-CHO-K1 line:

RNA was respectively extracted from the 220T-CD36-CHO-K1 line and the positive control Normal-CD36-CHO-K1 line in logarithmic growth phase. A target fragment of CD36 cDNA was amplified by RT-PCR using the first pair of PCR primers comprising the upstream primer YC-36F and the downstream primer YC-36R and using TaKaRa One step RNA PCR Kit (AMV). The amplification was carried out in ABI 9700 PCR machine, and the reaction system for amplification and the cycling parameters were as described in the step 1. 5 μL of the PCR product was stained by DNA green fluorescent dye (Beijing Tiandz Gene Technology Co., Ltd), and subjected to 1.5% agarose gel electrophoresis. With DL2000 Plus DNAMarker from Vazyme as a control, a band of specific PCR product was observed in a gel imaging system. The band of the PCR product was clear and specific. The size of the fragment was in agreement with the size of the product ZYT-CD36 cDNA fragment amplified in the step 1. 5 μL of the PCR product was sequenced. The cDNA sequencing results of the 220T-CD36-CHO-K1 line show that the sequence is in agreement with the sequence of the CD36 gene fragment in the transfected plasmid 220T-CD36-EGFP-pLV4/StripII-HIS10, as shown in FIG. 8. This suggests that the established 220T-CD36-CHO-K1 line can accurately express the mutant CD36 220C>T gene at a molecular level. The cDNA sequencing results of the positive control Normal-CD36-CHO-K1 line show that the sequence is in agreement with the sequence of the CD36 gene fragment in the transfected plasmid Normal-CD36-EGFP-pLV4/StripII-HIS10. This suggests that the established Normal-CD36-CHO-K1 line can accurately express normal CD36 gene at molecular level. The cDNA sequencing results of the negative control EGFP-pLV4-CHO-K1 line show that the sequence is in agreement with the sequence of the EGFP gene fragment in the transfected plasmid EGFP-pLV4/StripII-HIS 10. This suggests that the established EGFP-pLV4-CHO-K1 line can accurately express the EGFP gene at molecular level.

Figure 9:
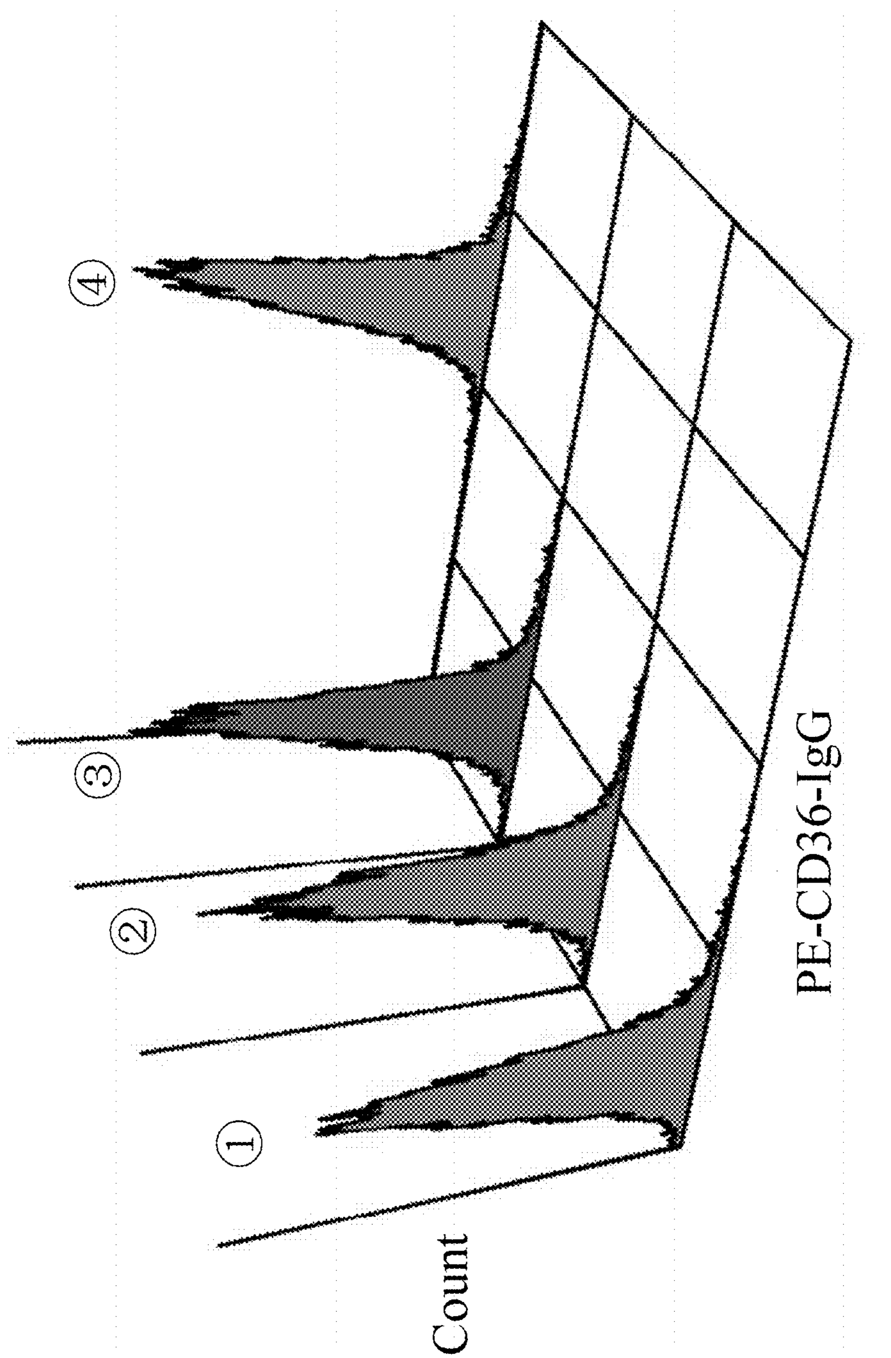
FIG. 9 shows the results of confirming CD36 protein expression in the eukaryotic CHO-K1 cell line (220T-CD36-CHO-K1 line) stably expressing the mutant CD36 gene (220C>T) by flow cytometry in Example 1, in which (1): the 220T-CD36-CHO-K1 line is negative in CD36 protein expression; (2): the negative control EGFP-pLV4-CHO-K1 line is negative in CD36 protein expression; (3) the blank control CHO-K1 line CD36 is negative in CD36 protein expression; and (4): the positive control NORMAL-CD36-CHO-K1 line is positive in CD36 protein expression.
Figure 10:
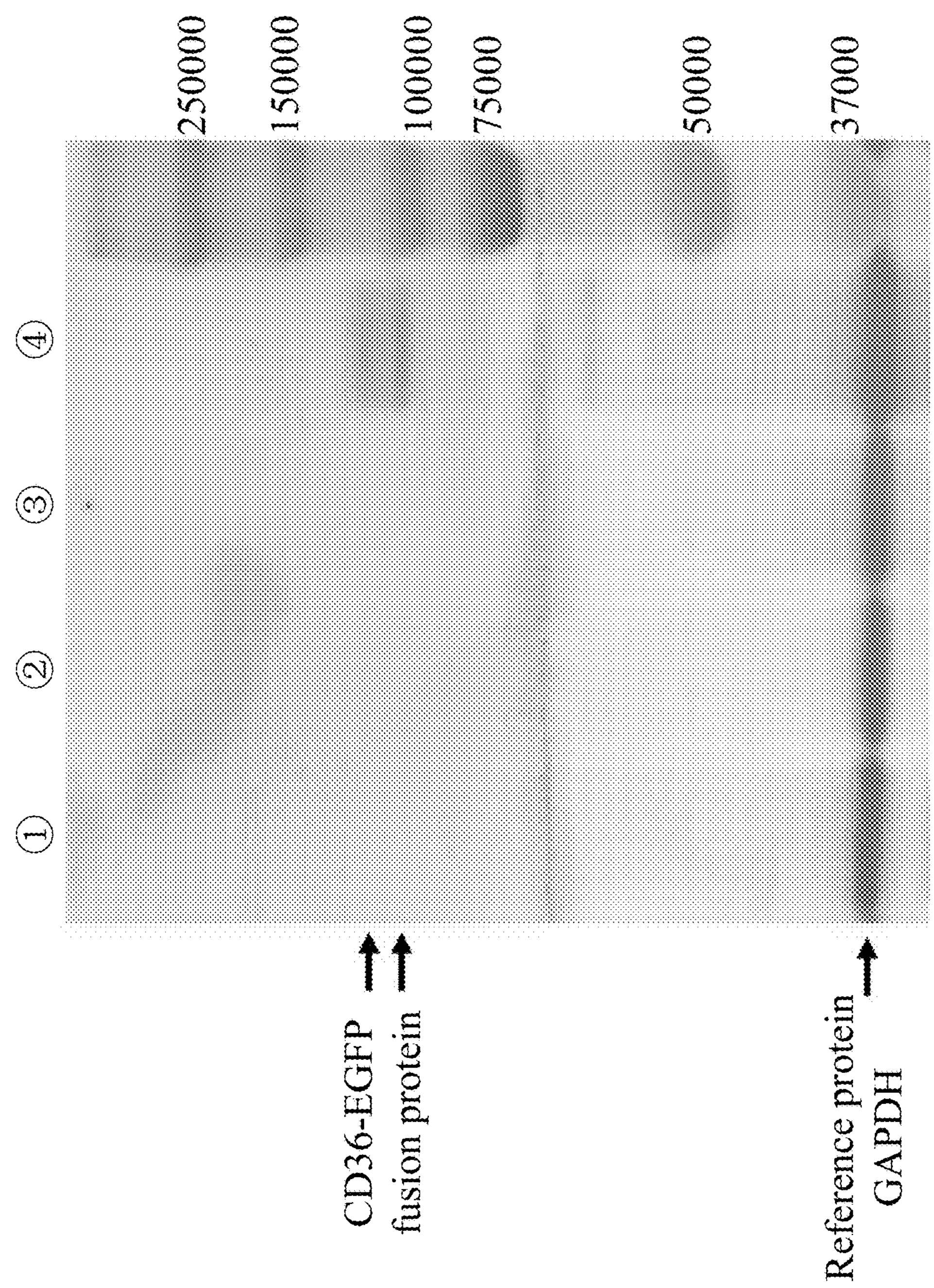
FIG. 10 shows the results of confirming CD36 protein expression in the eukaryotic CHO-K1 cell line (220T-CD36-CHO-K1 line) stably expressing the mutant CD36 gene (220C>T) by western-blotting in Example 1, in which (1)

The 220T-CD36-CHO-K1 line, the positive control Normal-CD36-CHO-K1 line, the negative control EGFP-pLV4-CHO-K1 line, and the blank control CHO-K1 line in logarithmic growth phase were collected, and detected for the CD36 expression by flow cytometry. The detection results are shown in FIG. 9, and indicate that the 220T-CD36-CHO-K1 line, the negative control EGFP-pLV4-CHO-K1 line, and the blank control CHO-K1 line are all negative in CD36 expression, and the positive control NORMAL-CD36-CHO-K1 line is positive in CD36 expression. Total membrance proteins were extracted from the several cell lines, and the expression of the CD36 protein by each cell line was detected by western-blotting. The detection results are shown in FIG. 10 and indicate that the 220T-CD36-CHO-K1 line, the negative control EGFP-pLV4-CHO-K1 line, and the blank control CHO-K1 line are negative in CD36 expression, and the positive control Normal-CD36-CHO-K1 line is positive in CD36 expression.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for establishing eukaryotic expression cell line of CD36 mutant gene that encodes CD36 deficiency, the method comprising:

(1) extracting total RNA from a whole blood sample derived from a CD36-deficient individual, and amplifying a coding sequence (CDS) in CD36 mRNA in the total RNA by Reverse Transcription PCR (RT-PCR) using a pair of primers, to obtain a cDNA sequence fragment of the mutant CD36 gene (MT-CD36 cDNA), wherein the pair of primers comprise an upstream primer YC-36F having a sequence of SEQ ID NO: 1, and a downstream primer YC-36R having a sequence of SEQ ID NO: 2;

2) using the MT-CD36 cDNA obtained in (1) as a template, a forward primer CD36-F2, and a reverse primer CD36-R3 to PCR-amplify a target sequence of MT-CD36-EGFP-1 comprising an EcoR 1 cleavage site and protective bases, a full-length coding sequence (CDS) excluding the terminator of CD36 cDNA, a fusion gene BamH I and protective bases, and a portion of a 5'-terminal sequence of an EGFP fluorescent reporter gene, wherein the forward primer CD36-F2 has a sequence of SEQ ID NO: 3, and the reverse primer CD36-R3 has a sequence of SEQ ID NO: 4;

using a eukaryotic plasmid pEGFP-N1 comprising the EGFP fluorescent reporter gene as a template, a forward primer EGFP-F4, and a reverse primer EGFP-R2 to PCR-amplify a target sequence of MT-CD36-EGFP-2 comprising a portion of the 3'-terminal fragment of the CD36 CDS cDNA, the fusion gene BamH I and protective bases, a full-length of the EGFP fluorescent reporter gene, and an XhoI cleavage site and protective bases, wherein the forward primer EGFP-F4 has a sequence of SEQ ID NO: 5, and the reverse primer EGFP-R2 has a sequence of SEQ ID NO: 6; and performing Gene Splicing by Overlap Extension PCR (SOE-PCR) using the MT-CD36-EGFP-1 and MT-CD36-EGFP-2 as templates and CD36-F2 and EGFP-R2 as primers to obtain a mutant gene sequence of MT-CD36-EGFP;

(3) constructing and amplifying a MT-CD36-EGFP-pLV4/StripII-HIS10 eukaryotic expression vector by ligating the MT-CD36-EGFP of (2) to a pLV4/StripII-HIS10 vector; the MT-CD36-EGFP-pLV4/StripII-HIS10 eukaryotic expression vector comprising the full-length CDS excluding the terminator of the mutant CD36 cDNA and the EGFP fluorescent gene; and (4) transfecting the MT-CD36-EGFP-pLV4/StripII-HIS10 eukaryotic expression vector into a CHO-K1 cell line by using virus-mediated transfection of eukaryotic cells, and screening and constructing a eukaryotic cell line MT-CD36-CHO-K1 expressing the mutant CD36 gene that encodes CD36 deficiency.

2. The method of claim 1, wherein in (1), a RT-PCR amplification region covers the coding sequence (CDS) of CD36 mRNA, and a plurality of mutant CD36 genes within a linker region of 5'-terminal and 3'-terminal primer binding regions of the template is obtained through the RT-PCR amplification; and for the length of the fragment amplified by the RT-PCR amplification of the mutant CD36 gene, if the target mutant CD36 gene amplified is a gene with point mutations, the length of the amplified fragment is 1432 bp, and if the target mutant CD36 gene amplified is a mutant gene with base insertions or deletions, the length of the amplified fragment is increased or decreased on the basis of 1432 bp by the base number inserted or deleted.

3. The method of claim 1, wherein the CD36-F2 comprises the EcoR 1 cleavage site and protective bases; the CD36-R3 comprises the portion of the 5'-terminal promoter region sequence of the EGFP fluorescent reporter gene and the fusion gene BamH I and protective bases; and for the length of the target sequence of MT-CD36-EGFP-1, when the mutant CD36 gene comprises point mutations, the length of the target sequence of MT-CD36-EGFP-1 is 1441 bp, and when the mutant CD36 gene comprises base insertions or deletions, the length of the target sequence of MT-CD36-EGFP-1 is increased or decreased on the basis of 1441 bp by the base number inserted or deleted;

the length of the target sequence of MT-CD36-EGFP-2 is 753 bp; and when the mutant CD36 gene comprises point mutations, the length of the amplified sequence of MT-CD36-EGFP is 2165 bp, and when the mutant CD36 gene comprises base insertions or deletions, the length of the amplified sequence of MT-CD36-EGFP is increased or decreased on the basis of 2165 bp by the base number inserted or deleted.

* * * * *